United States Patent
Kevil et al.

(10) Patent No.: US 11,883,426 B2
(45) Date of Patent: Jan. 30, 2024

(54) TREATMENT FOR METHAMPHETAMINE CARDIOVASCULAR DISEASE

(71) Applicant: Board of Supervisors of Louisiana State University and Agricultural and Mechanical College, Baton Rouge, LA (US)

(72) Inventors: Christopher Kevil, Shreveport, LA (US); Gopi K. Kolluru, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 17/397,973

(22) Filed: Aug. 9, 2021

(65) Prior Publication Data

US 2022/0040222 A1 Feb. 10, 2022

Related U.S. Application Data

(60) Provisional application No. 63/063,225, filed on Aug. 8, 2020.

(51) Int. Cl.
*A61K 31/724* (2006.01)
*A61K 45/06* (2006.01)
*C12N 9/88* (2006.01)

(52) U.S. Cl.
CPC ............ *A61K 31/724* (2013.01); *A61K 45/06* (2013.01); *C12N 9/88* (2013.01); *C12Y 404/01001* (2013.01)

(58) Field of Classification Search
CPC ................. A61K 31/724; A61K 38/51; A61P 9/00–14; C12N 9/88
See application file for complete search history.

(56) References Cited

FOREIGN PATENT DOCUMENTS

CN 101940785 A * 1/2011
WO WO-2019094383 A1 * 5/2019 ............ A61K 31/00

OTHER PUBLICATIONS

Zhang, X. et al "N-acetylcysteine amide protects against methamphetamine-induced tissue damage . . . " Hum. Exp. Toxicol., vol. 31, No. 9, pp. 931-944. (Year: 2012).*
Lord, K. et al "Oxidative stress contributes to methamphetamine-induced left ventricular dysfunction" Cardiovasc. Res., vol. 87, pp. 111-118. (Year: 2010).*
Yu, X. et al "Hydrogen sulfide as a potent agent" Clin. Chim. Acta, vol. 437, pp. 78-87. (Year: 2014).*
Kashfi, K. et al "biology adn therapeutic potential hydrogen sulfide . . . " Biochem. Pharmacol., vol. 86, pp. 689-703. (Year: 2013).*
Deng, C. et al "Supramolecular hosts as in vivo sequestration agents . . . " Chem. Soc. Rev., vol. 49, pp. 7516-7532. (Year: 2020).*
Machine translation of CN 101940785A. (Year: 2011).*

* cited by examiner

*Primary Examiner* — Leigh C Maier
(74) *Attorney, Agent, or Firm* — Jones Walker LLP

(57) ABSTRACT

A method of treating or preventing methamphetamine related endothelial dysfunction in a patient comprising administering to the patient an effective dose of a pharmacologic composition; the composition comprising a therapeutic, the therapeutic including a hydrogen sulfide ($H_2S$) donor, or a salt, solvate, ester, amide, clathrate, stereoisomer, enantiomer, prodrug or analogs thereof. The $H_2S$ donor may be one of sodium sulfide, diallyl trisulfide, diallyl disulfide, allicin, sugammadex, sulfanilamide, disulfiram, sulfonamide, sulfonates, sulfoxides, persulfides, polysulfides, and sulfones. The $H_2S$ donor may be sugammadex. The $H_2S$ donor may be administered in a dosage of between 0.5 mg/kg and 10.0 mg/kg.

16 Claims, 13 Drawing Sheets

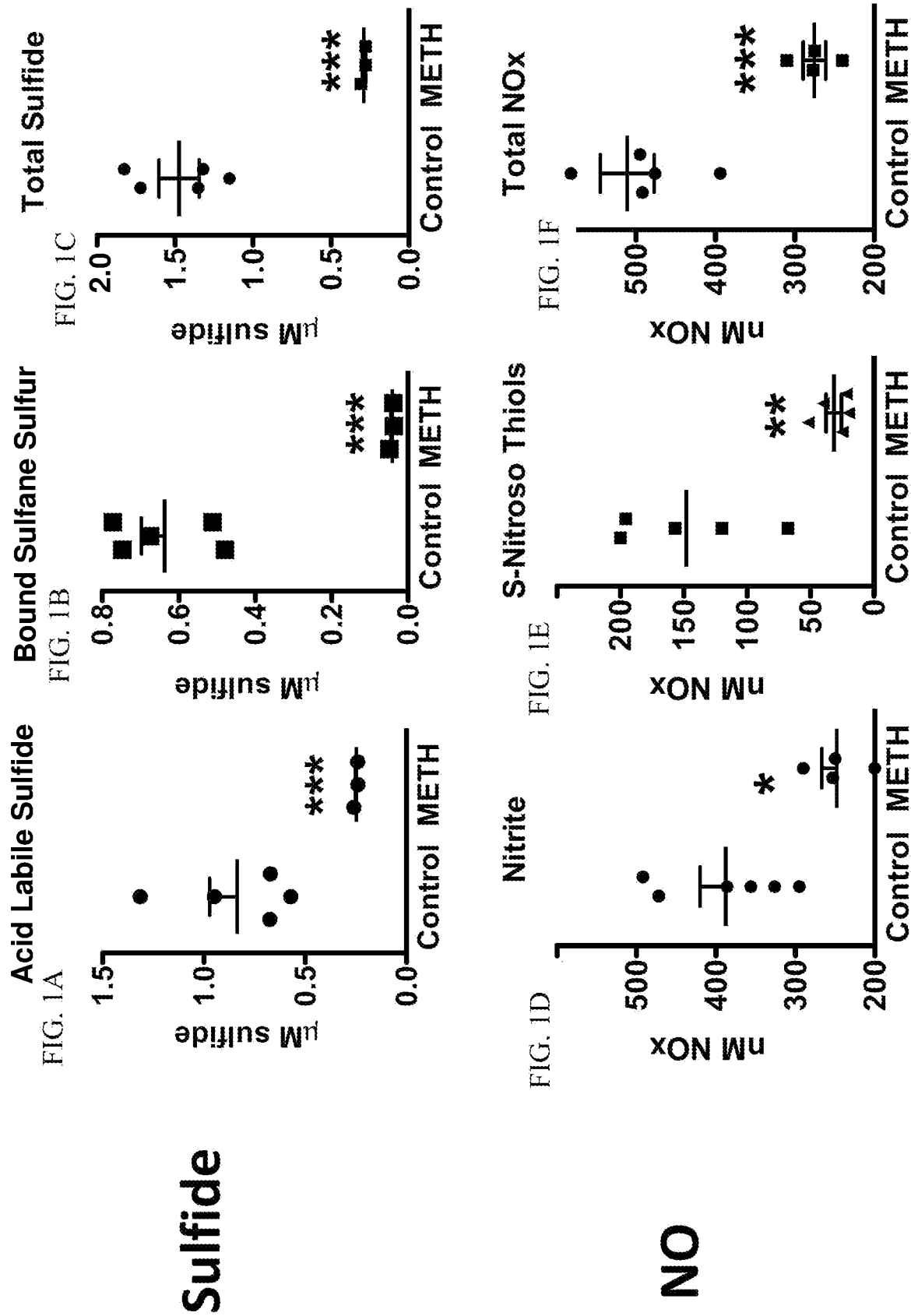

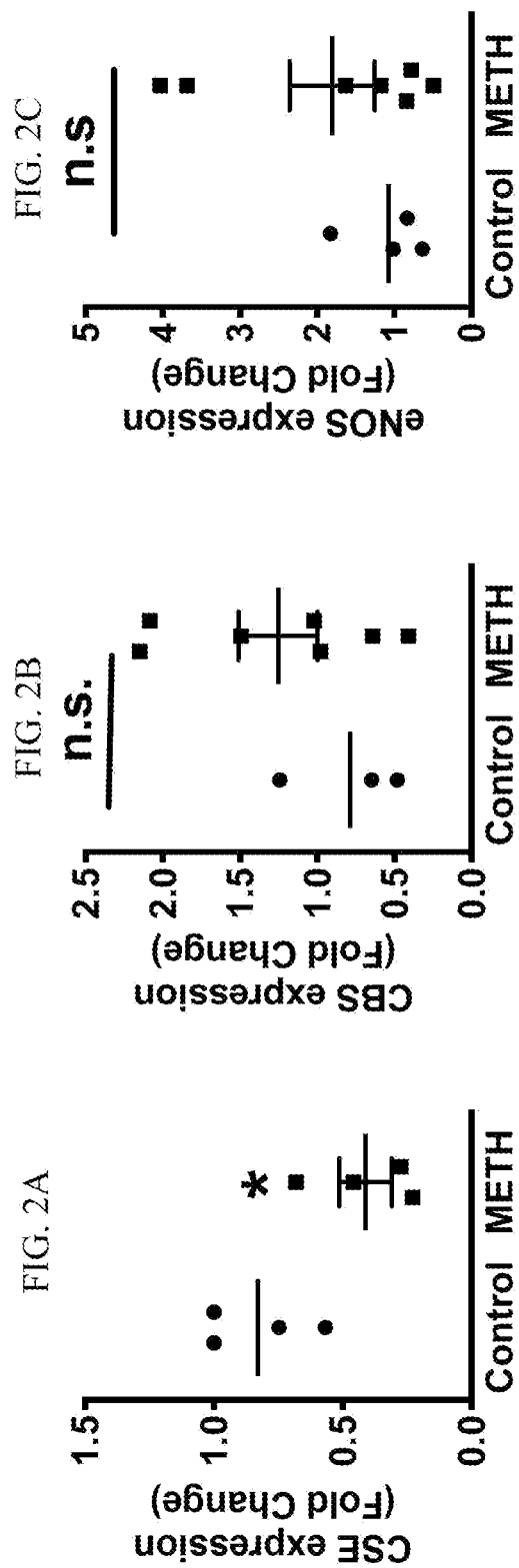
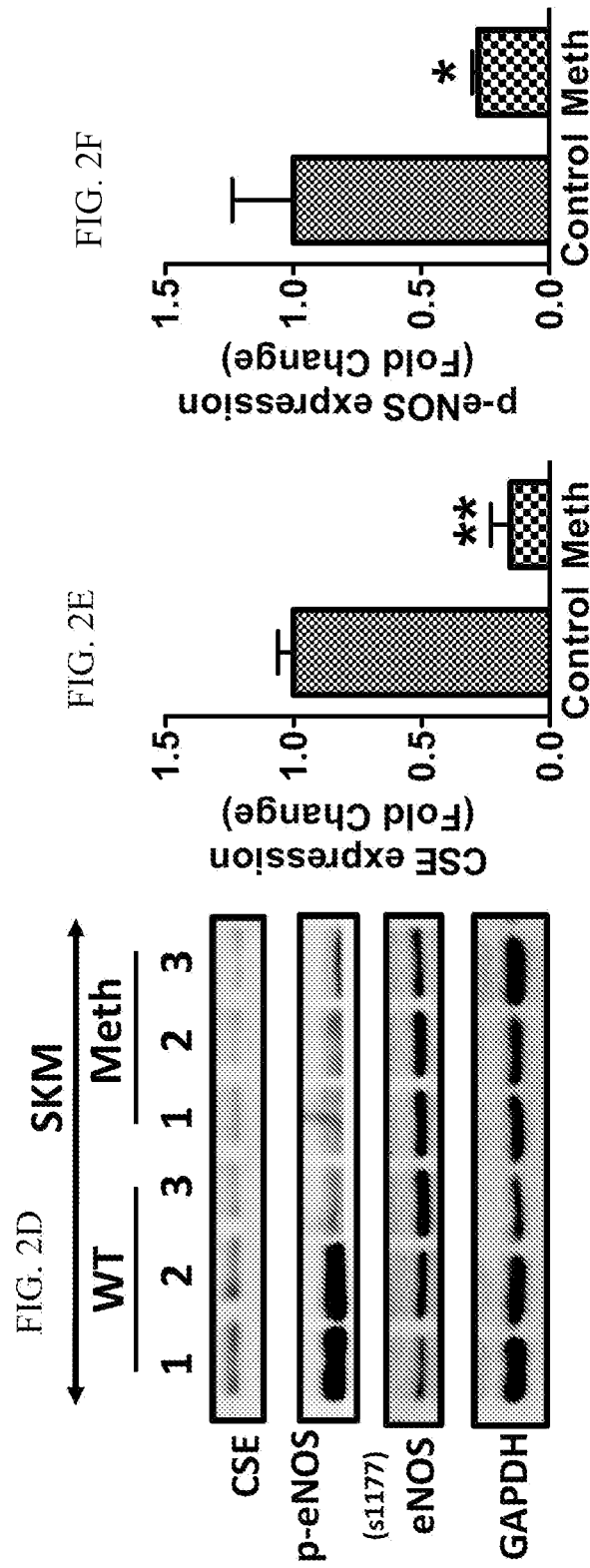

DAPI
CD31
CSE

TREATMENT FOR METHAMPHETAMINE CARDIOVASCULAR DISEASE

CROSS REFERENCE TO RELATED APPLICATIONS/PRIORITY

The present invention claims priority to U.S. Provisional Patent Application No. 63/063,225 filed Aug. 8, 2020, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

Methamphetamine was first synthesized in 1893 by the Japanese chemist Nagai Nagayoshi. Methamphetamine is a more potent version of amphetamine, first synthesized in Germany in 1887. During World War II, the Axis and Allied forces used methamphetamine and amphetamine to extend wakefulness, and in the postwar period both agents were used as diet pills, before their destructive and addictive nature were fully understood. Methamphetamine is available in various forms including liquid, powder, and as a crystalline substance, first synthesized in Japan by Akira Ogata in 1919, which can be smoked. Both when injected intravenously as well as when smoked, high levels of the drug are rapidly achieved in the circulation. The main effects are neurocognitive-both a euphoric and energized state as well as psychosis, depression, and other neuropsychiatric and cognitive sequelae (dizziness, anxiety, apathy, depression, aggression, cognitive impairments, personality changes, mania, psychosis). Methamphetamine abusers typically go on "meth binges" lasting days.

Methamphetamine (methamphetamine) is a markedly addictive illicit drug and has severe psychological, and social risks that affect different ethnic groups worldwide. Statistics from the National Survey on Drug Use and Health (NSDUH) reveal that an estimated 24.6 million Americans ages 12 or older have used methamphetamine in their lifetimes for non-medical reasons. There are significant social and health hazards associated with methamphetamine usage. Recent studies have revealed increased prevalence of cardiovascular disease (CVD) including hypertension, vasospasm, cardiomegaly, arrhythmias, left ventricular hypertrophy, myocardial infarction, and coronary artery disease at a young age. Methamphetamine has effects on multiple organ systems including cardiovascular complications that are the second leading cause of death due to methamphetamine use. Importantly, methamphetamine use disproportionally increases cardiovascular-related morbidity and mortality in up to three-fourths of its users. Several clinical and postmortem studies associate the use of methamphetamine with cardiovascular disease leading to death. However, the understanding of methamphetamine-related cardiovascular implications and the underlying molecular mechanisms remain poorly understood, which could explain why some traditional cardiac medications prescribed to methamphetamine users to treat cardiovascular disease have been ineffectual.

SUMMARY

Wherefore, it is an object of the present invention to overcome the above-mentioned shortcomings and drawbacks associated with the current technology.

The presently disclosed invention is related to therapeutics and methods of treating or preventing methamphetamine related endothelial dysfunction in a patient comprising administering to the patient an effective dose of a pharmacologic composition the composition comprising a therapeutic the therapeutic including a hydrogen sulfide ($H_2S$) donor. According to a further embodiment the $H_2S$ donor is one of sodium sulfide, diallyl trisulfide, diallyl disulfide, allicin, sugammadex, sulfanilamide, disulfiram, sulfonamide, sulfonates, sulfoxides, persulfides, polysulfides, and sulfones. According to a further embodiment the $H_2S$ donor is sugammadex. According to a further embodiment the $H_2S$ donor is administered in a dosage of between 0.5 mg/kg and 10.0 mg/kg. According to a further embodiment the $H_2S$ donor is administered exactly once in a dosage period, the dosage period being between 1 day and 30 days. According to a further embodiment the dosage period is seven days. According to a further embodiment the therapeutic is administered in one of oral, intravenous, and transdermal pathways. According to a further embodiment the therapeutic is administered orally. According to a further embodiment the therapeutic is administered intravenously. According to a further embodiment the patient has one of atherosclerosis, hypertension, myocardial infarction, and diabetes, and cardiovascular disease, or a precondition thereof. According to a further embodiment, the composition further comprises one of cystathionine gamma lyase or a salt, solvate, ester, amide, clathrate, stereoisomer, enantiomer, prodrug, or analogs thereof.

The presently disclosed invention further relates to therapeutics and methods of treating an endothelial dysfunction related disease in a methamphetamine patient comprising administering to the patient an effective dose of a pharmacologic composition, the composition comprising a therapeutic, and the therapeutic including a hydrogen sulfide ($H_2S$) donor. According to a further embodiment, the related disease is one of atherosclerosis, hypertension, myocardial infarction, and diabetes, and cardiovascular disease, or a precondition thereof. According to a further embodiment, the method further comprises administering a second, non-$H_2S$ donor therapeutic for the treatment of the related disease.

The presently disclosed invention further relates to methods of treatment and pharmaceutical compositions comprising a therapeutic, the therapeutic including a hydrogen sulfide ($H_2S$) donor formulated for one of oral and peritoneal administration and being in a dosage of between 1.0 mg and 100.0 mg of $H_2S$ donor. According to a further embodiment, the composition includes an exact dosage of between 5.0 mg and 60 mg of the $H_2S$ donor, and between 10 mg and 30 mg of the $H_2S$ donor. According to a further embodiment, composition further comprises cystathionine gamma lyase or a salt, solvate, ester, amide, clathrate, stereoisomer, enantiomer, prodrug, or analogs thereof. According to a further embodiment, the composition includes an exact dosage of between 1.0 mg and 100 mg, 5.0 mg and 60 mg, and between 10 mg and 30 mg of cystathionine gamma lyase or a salt, solvate, ester, amide, clathrate, stereoisomer, enantiomer, prodrug, or analogs thereof.

The present invention relates to pharmaceutical compositions of a therapeutic (e.g., a hydrogen sulfide ($H_2S$) donor), or a pharmaceutically acceptable salt, solvate, ester, amide, clathrate, stereoisomer, enantiomer, prodrug or analogs thereof, and use of these compositions for the treatment of endothelial dysfunction and diseases and conditions that are causes of endothelial dysfunctions, such as cardiovascular complications including atherosclerosis, hypertension, myocardial infarction, and diabetes, and cardiovascular disease. Examples of $H_2S$ donors include sodium sulfide, diallyl tri sulfide, diallyl disulfide, allicin, sugammadex, sulfanilamide, disulfiram, sulfonamide, sulfonates, sulfoxides, persulfides, polysulfides, and sulfones.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In some embodiments, the condition is an endothelial dysfunction.

In certain embodiments, the endothelial dysfunction is mild to moderate endothelial dysfunction.

In further embodiments, the endothelial dysfunction is moderate to severe endothelial dysfunction.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more additional therapeutic agents for the treatment or prevention of the endothelial dysfunction.

In some embodiments, the therapeutic, or a pharmaceutically acceptable salt, solvate, or prodrug thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 M (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active agent (e.g., a therapeutic as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably include a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 M, 0.1-5.0 µM, or 0.1-1 µM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release" includes where the agent (e.g., therapeutic), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing a compound described herein (e.g., an $H_2S$ donor, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal.

Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., an endothelial dysfunction). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of therapeutic. A thorough discussion is provided in T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, each of which is incorporated herein by reference. Preferably, prodrugs of the compounds of the present invention are pharmaceutically acceptable.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also include delaying the onset of, impeding, or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" includes the amount of therapeutic present in the plasma of a treated subject (e.g., as measured in a rabbit using an assay described below or in a human).

The disclosed invention further relates to the identification of hydrogen sulfide and CSE as a key target of methamphetamine dependent cardiovascular dysfunction.

The disclosed invention further relates to disclosure of molecular mechanisms involved in methamphetamine reduction of $H_2S$ via inhibition of CSE gene expression.

The disclosed invention further relates to disclosure that methamphetamine decreases $H_2S$ levels, which then contributes to NO dysregulation.

The disclosed invention further relates to creating the therapeutic approaches and verifying that both pharmacologic and genetic therapeutic approaches attenuate methamphetamine endothelial dysfunction.

The disclosed invention further relates to experimentally showing the clinical utility of $H_2S$ based therapeutic approaches for cardiovascular dysfunction in methamphetamine abusers.

The disclosed invention further relates to the discovery that methamphetamine increases pro-aging gene expression.

The disclosed invention further relates to the discovery that Sugammadex increases plasma sulfide levels in wild type and CSE knockout mice to therapeutically significant levels at fractional doses.

The disclosed invention further relates to the discovery that Sugammadex increases human plasma sulfide levels and CSE activity in humans to therapeutically significant levels at fractional doses.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that while the accompanying drawings are to scale, the emphasis is instead placed on illustrating the principles of the invention. The invention will now be described, by way of example, with reference to the accompanying drawings in which:

FIGS. 1A-1F show methamphetamine decreases plasma total sulfide and NO metabolites in mice;

FIGS. 2A-2F show methamphetamine decreases murine CSE expression and eNOS phosphorylation;

DETAILED DESCRIPTION

Figure 3A:
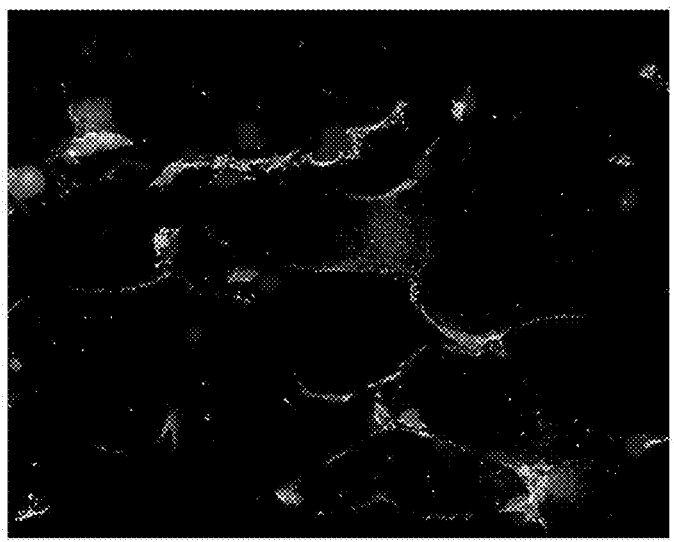
FIGS. 3A-3C show methamphetamine decreases CSE Protein Expression in Mouse muscle tissue.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The terms "comprise(s)," "include(s)," "having," "has," "can," "contain(s)," and grammatical equivalents and variants thereof, as used herein, are intended to be open-ended transitional phrases, terms, or words that do not preclude the possibility of additional acts or structures, are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. The singular forms "a," "and" and "the" include plural references unless the context clearly dictates otherwise. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number) (a second number)," this means a range whose lower limit is the first number and whose upper limit is the second number. For example, 25 to 100 mm means a range whose lower limit is 25 mm, and whose upper limit is 100 mm.

The embodiments set forth the below represent the necessary information to enable those skilled in the art to practice the invention and illustrate the best mode of practicing the invention. For the measurements listed, embodiments including measurements plus or minus the measurement times 5%, 10%, 20%, 50% and 75% are also contemplated. For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

In addition, the invention does not require that all the advantageous features and all the advantages of any of the embodiments need to be incorporated into every embodiment of the invention.

Turning now to FIGS. 1A-14C, a brief description concerning the various components of the present invention will now be briefly discussed.

Vascular endothelium plays a central role in the maintenance of cardiovascular homeostasis. Disruption of endothelial function, clinically referred to as endothelial dysfunction, is a key pathophysiological mediator of nearly all cardiovascular disease. Endothelial dysfunction is a hallmark prerequisite of cardiovascular complications including atherosclerosis, hypertension, myocardial infarction, and diabetes. Methamphetamine can have adverse and potentially fatal effects on arteries and blood vessels, which results in increased blood pressure, inflammation and cardiovascular dysfunction including atherosclerosis. Methamphetamine induces pro-inflammatory signaling responses and increases the production of reactive oxygen species that are detrimental to the cardiovascular system. While methamphetamine may induce oxidative stress contributing to cardiovascular dysfunction, the specific mechanisms, reactive oxygen species involved, and the molecular trigger of events leading to this response remained completely unknown in the current technology.

Hydrogen sulfide ($H_2S$) and nitric oxide (NO) are gaseous signaling molecules that serve important roles in regulating endothelial and cardiovascular health. Cystathionine gamma lyase (CSE) and $H_2S$ play critical regulatory roles in various cardiovascular pathophysiological functions including vasorelaxation, protection from oxidative damage and cytoprotection. Vascular $H_2S$ bioavailability directly influences NO bioavailability. However, the underlying molecular mechanisms of methamphetamine mediated endovascular dysfunction remained elusive in the current technology. Additionally, no information previously existed regarding the role of CSE/$H_2S$/NO alterations in clinical vascular disease conditions of methamphetamine users. Also, prolonged exposure of methamphetamine can induce pro-oxidant and pro-inflammatory events and signaling that trigger endothelial dysfunction, aggravating the cardiovascular complications.

Importantly, previous studies aimed at understanding a relationship between methamphetamine and NO have been focused on neuronal injury with no clear understanding of impacts in vascular function. This current disclosure describes the molecular mechanisms underlying methamphetamine-mediated $H_2S$/NO signaling, oxidative stress and inflammation leading to vascular dysfunction, and therapeutics and methods of treatment based on such discoveries.

Materials and Methods. 2.1 Chemicals and Reagents: Chemicals and tissue culture reagents, including Methamphetamine hydrochloride (methamphetamine) were obtained from Sigma unless otherwise noted. Anhydrous sodium sulfide was purchased from Alfa-Aesar Inc. Anti-CD31 antibody was from BD Biosciences (San Jose, Calif., USA), and anti-α-SMA antibody was obtained from Sigma-Aldrich. VECTASHIELD PLUS DAPI was from Vector Laboratories. All secondary fluorophore-labeled antibodies were obtained from Jackson Immunoresearch Inc (West Grove, Pa., USA). Human umbilical vein endothelial cells (HUVECs) were from Lifeline Cell Technology, CA, USA.

2.2 Cell culture and treatments: Human umbilical vein endothelial cells (HUVECs) were purchased from Lifeline Cell Technology (Cat. No. FC-0044) and cultured in VascuLife® Basal Medium (Cat. No. LM-0002) supplemented with the appropriate LifeFactors® Kit (No. LL-0003). All cells were grown in tissue culture flasks at 37° C. and 5% $CO_2$. HUVECs from passages 2-4 were used in the experiments.

2.3 Mouse model and treatment routes: Twelve-week-old male WT (C57BL6/J) and CSE Tg male mice were used to study 'Binge' methamphetamine administration effects on endovascular function. Mice were randomly assigned to different experimental groups by one investigator and were treated and evaluated by a second blinded investigator. NaHS drinking solutions were made by dissolving the appropriate amount of NaHS with the appropriate volume of tap water for final NaHS concentration (30 µM). Sulfide donor, $Na_2S$ (30 µM) or just water was administered in the drinking water of mice treated with either methamphetamine or saline during the length of the study. Mice were housed at the Louisiana State University Health Sciences Center-Shreveport animal resources facility, which is accredited by the Association for Assessment and Accreditation of Laboratory Animal Care International. All animal studies were approved by the LSU Institutional Animal Care and Use Committee (LSU IACUC Protocol #P-08-021) and in accordance with the Guide for the Care and Use of Laboratory Animals published by the National Institutes of Health.

2.4 'Binge and crash' mouse methamphetamine model: Twelve-week-old male WT (C57BL6/J) male mice were used for these experiments. Mice were exposed to methamphetamine according to a known protocol that models binge methamphetamine exposure in humans. C57BL/6 male mice received 0-6 mg/kg methamphetamine (Methamphetamine HCl, Sigma-Aldrich, St. Louis, Mo.) through subcutaneous (s.c.) injection five days in a week for four weeks. Methamphetamine was dissolved in a sterile saline (Sigma-Aldrich) solution (0.9% w/v NaCl). Vehicle treated mice received the same volume of saline at all-time points for four weeks. Briefly, methamphetamine-exposed and saline-control mice were injected subcutaneously with methamphetamine or saline in a volume of 5 ml/kg with an insulin syringe. Alternating sites of injection were used to avoid any possible damage to tissue and possible stress of the animal. The dose of methamphetamine was escalated over the course of the first cycle, which occurs during the first week of injections (days 1-5) followed by three weeks of repeated cycles of meth injections (days 8-12, 15-19, and 22-26). Mice received 4 injections per day, 2 hours apart with doses of meth including 0, 1, 2, 3, 4, 5, and 6 mg/kg subcutaneously. At the end of the 4 weeks, mice were sacrificed by isoflurane overdose, plasma and tissue were harvested.

2.5 Flow mediated dilation (FMD): Vascular function was determined by mouse FMD. Experimental cohorts of Control (saline), methamphetamine (0-6 mg/kg) with or without sulfide (30 µM), were treated for 4 weeks, and subjected to FMD. Briefly, mice were anesthetized with isoflurane and fur was removed from the hindlimbs. The animals were then placed on a warmed ultrasound table equipped with ECG. A vascular occluder (5 mm diameter, Harvard Apparatus) was placed around the proximal hindlimb to induce transient occlusion of the vessels of the distal hindlimb as an ischemic trigger. The Doppler ultrasound probe (VEVO 3100, VisualSonics) was manually aligned over the femoral artery, distal to the occluder, to take baseline recordings of the blood vessel for diameter (M mode) and mean velocity (PW mode). The vascular occluder was inflated manually with an air-filled syringe for 1-minute, and deflated. Measurements of diameter and blood flow velocity were recorded for 180s at 30s intervals. The recorded loops were analyzed by Vevo LAB analysis software.

2.6 Human blood collection: Human subjects were interviewed, and medical record data were collected for analysis of methamphetamine-use. Blood samples were collected from already-established catheterization into 6 mL BD vacutainer tubes with lithium heparin. Samples were transported to the lab within 15 min on ice and were centrifuged at 1500 RCF for 4 min at 4° C.

2.7 Measurement of biological pools of $H_2S$: Plasma samples from mouse and human subjects were analyzed for free sulfide, acid-labile sulfide (ALS), bound sulfane sulfur (BSS), and total sulfide levels using the monobromobimane (MBB) method as the inventors have previously reported. Free sulfide was measured using 50 µl of plasma with MBB; whereas for detection of ALS and BSS, 50 µl of plasma was added separately into two sets of 4 mL BD vacutainer tubes. Four hundred fifty microliters of 100 mM phosphate buffer (pH 2.6, 0.1 mM DTPA) was added to one tube [acid labile reaction] and 450 µl of 100 mM phosphate buffer (pH 2.6, 0.1 mM DTPA) plus 1 mM TCEP was added to the second tube [total sulfide reaction]. Following a 30-min incubation on a nutator, the reaction liquid was removed, and the evolved sulfide gas subsequently trapped by adding 500 µl of 100 mM Tris-HCl buffer (pH 9.5, 0.1 mM DTPA) into the BD vacutainer tube and incubated again for 30 min on a nutator mixer. The trapping solutions were removed, and sulfide levels measured using the MBB method as the inventors have previously reported. Determination of ALS was made by reacting plasma samples with acidic phosphate buffer alone and subsequent trapping of evolved sulfide. Measurement of BSS was determined by subtracting the acid labile value from the total sulfide protocol containing TCEP reductant treatment under acidic conditions. Total sulfide levels were directly obtained from the total sulfide reaction.

2.8 NO metabolite measurements: NO metabolites (NOx) were measured using an ozone-based chemiluminescent assay (Sievers Nitric Oxide Analyzer 280i, Weddington, N.C.) as described previously. Plasma and skeletal muscle tissue samples were collected in NO preservation buffer (1.25 mol/L potassium ferricyanide, 56.9 mmol/L N-ethylmaleimide, 6% Nonidet P-40 substitute in PBS). Aliquots of samples were tested for free nitrite and sulfanilamide resistance following addition of an acidic sulfanilamide solution to a final concentration of 0.5% v/v and sitting in the dark for 15 min prior to injection into the analyzer.

2.9 Cystathionine γ-lyase (CSE) activity measurement: CSE activity was measured as previously reported. Plasma or tissue lysates were incubated with 2 mM cystathionine, 0.25 mM pyridoxal 5'-phosphate in 100 mM Tris-HCl buffer (pH 8.3) for 60 min at 37° C. 10% Trichloroacetic acid was added into reaction mixture. After centrifugation, the supernatant was mixed with 1% ninhydrin reagent and incubated for 5 min in a boiling-water bath. After heating, the solution was cooled on ice for 2 minutes and color reaction development measured 20 minutes at 455 nm using a spectrophotometer (Biotek). CSE activity was assessed by cystathionine consumption and enzyme activity expressed as fold change calculated from nanomoles of cystathionine consumed per mg of total protein per hour of incubation.

2.10 Western blot analysis: Mouse skeletal muscle tissues were homogenized in a solution containing 50 mM Tris buffer (pH 7.4), 2 mM EDTA, 5 mM EGTA, 0.1% SDS, a protease inhibitor cocktail (Roche, Indianapolis, Ind.), and phosphatase inhibitor cocktail type I and II (Sigma, Saint Louis, Mo.). Homogenates were centrifuged at 500×g for 15 min and supernatants were collected. Protein concentrations were analyzed using the Bradford protein assay (BIORAD, Hercules, Calif.). Proteins were separated using 10% SDS-PAGE (Bio-Rad, Hercules, Calif.) and transferred onto PVDF membranes, and incubated with antibodies against CSE #12217-1-AP (Fisher Scientific), eNOS #9572, phospho-eNOS #9750 and GAPDH #2118 (Cell Signaling). Chemiluminescent bands were detected and quantified using NIH Image J software.

2.11 Quantitative PCR: Samples were stored in TRIzol reagent (Thermo Fisher Scientific Inc., Waltham, Mass., USA) and RNA was isolated using phenol:chloroform extraction procedure. RNA concentration and purity were evaluated with a NanoDrop 2000 spectrometer (Thermo Fisher Scientific Inc., Waltham, Mass., USA). RNA samples with an absorbance ratio OD 260/280 between 1.8-2.1 and OD 260/230 between 2-2.2 were used for further analysis. Single-stranded cDNA was synthesized using ISCRIPT cDNA synthesis kit (Bio-Rad, Hercules, Calif., USA), from 1 µg of total RNA in a final volume of 20 µL. cDNA was stored at −20° C. for future use. Quantitative PCR reactions were performed using the universal SYBR Green Supermix (Bio-Rad, CA, USA) on a CFX96 thermal cycler with Bio-Rad CFX Manager software (Bio-Rad, Hercules, Calif., USA). 50 ng of cDNA were used for each reaction. The reactions for each sample were run in triplicate. The mean threshold cycle (Ct) values for each serial dilution was plotted against the logarithm of the cDNA dilution factor.

2.11 Immunohistochemistry: Immunohistochemistry staining with anti-CD31 and anti-CSE antibodies was performed with nuclear stain 4',6-diamidine-2'-phenylindole dihydrochloride (DAPI), as the inventors have previously described.

2.12 Oxidative Stress measurement: Levels of oxidative stress were measured by staining skeletal muscle tissue sections with 5 µM Dihydroethidium (DHE; Sigma-Aldrich, CA USA) and visualized using a NIKON ECLIPSE Ti-E microscope (Nikon Instruments Inc., Melville, N.Y.) for image acquisition. Simple PCI software version 6.0 (Compix Inc., Sewickley, Pa., USA) was used to analyze the area.

2.12 Statistical Analysis: Data were reported as mean±standard error of the mean (SEM) for all groups. Statistical analysis was performed with GraphPad Prism using Student's t-test, one-way ANOVA and two-way ANOVA with Tukey post-hoc test, Mann-Whitney or Kruskal-Wallis analysis of variance with Dunn's multiple-comparison tests. A p-value of <0.05 was considered to be statistically significant.

Figure 6A:
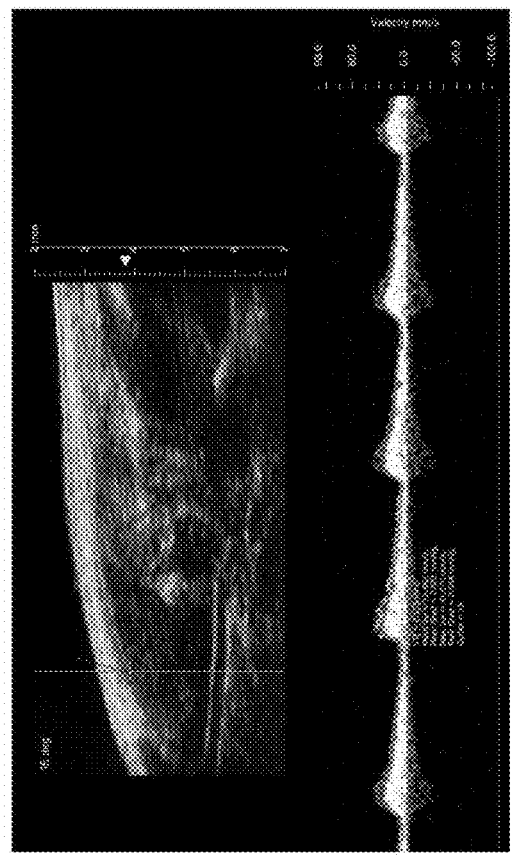
FIGS. 6A-6D show methamphetamine causes endothelial cell dysfunction in mice.
Figure 6B:
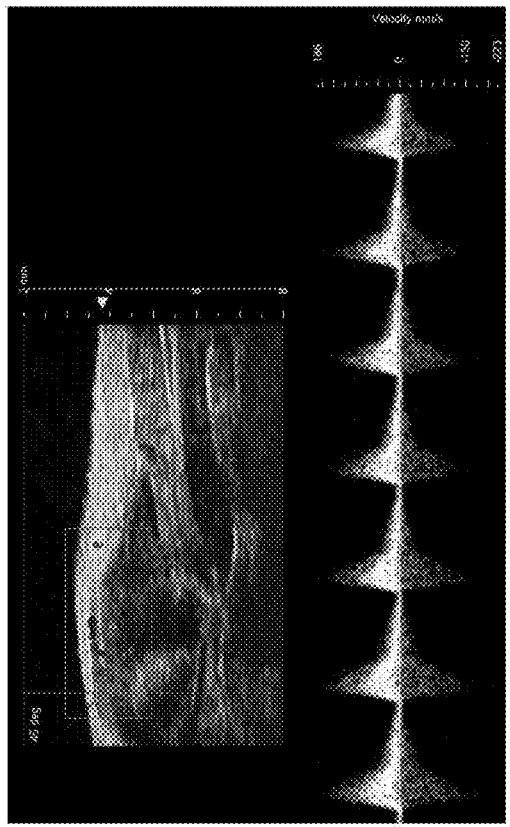
Figure 6D:
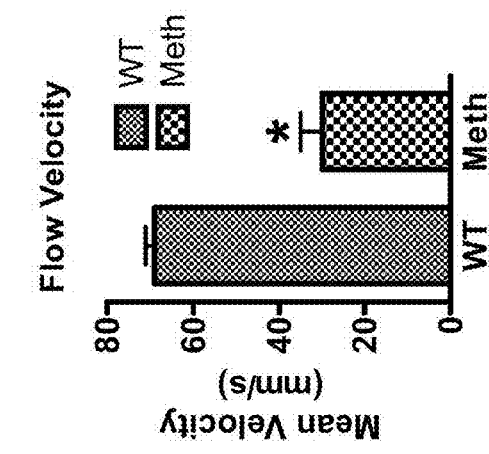
Figure 6C:
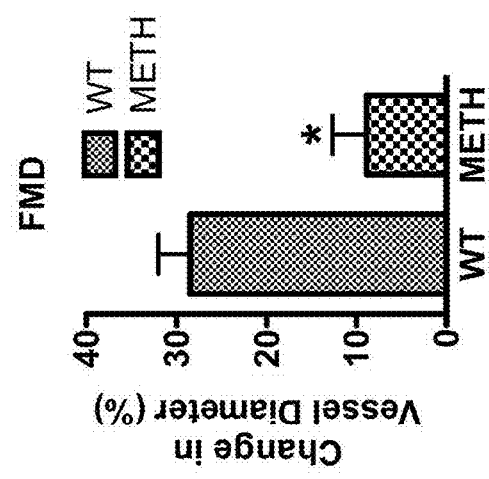

Results: Methamphetamine experimental 'binge and crash' model causes endothelial cell dysfunction. In the systemic circulation, terminal arteries are crucial for regulating blood flow to all organs throughout the body. Moreover, arteries and blood vessels are significantly affected by methamphetamine use resulting in cardiovascular dysfunction and central nervous system damage. Methamphetamine induces vasoconstriction that reduces essential blood flow, increases blood pressure and blood clotting, which can lead to increased bleeding in the brain and stroke and may cause abnormalities in the heart, the inventors have used a non-invasive flow mediated dilation (FMD) model in mice to assess endothelial function of femoral arteries at the end of the 4-week 'binge and crash' methamphetamine treatment protocol. The mouse FMD model entails temporary 1-minute occlusion of limb blood flow using an inflatable cuff followed by doppler ultrasound measurement of changes in blood flow following release of the cuff. Real time measurements of vascular diameter changes and mean blood flow velocity are collected reflecting changes in endovascular function and health. FIGS. 6A and 6B show reactive doppler blood flow responses between saline control versus methamphetamine treated mice, respectively. FIG. 6C shows that methamphetamine treated mice have significantly blunted flow mediated vasodilation responses at (what timepoint?) compared to saline treated control mice. Lastly, panel 6D illustrates that methamphetamine treatment significantly blunts mean blood flow velocity recovery after occlusion removal. These data show that methamphetamine elicits endothelial dysfunction in response to flow mediated vasodilation.

Methamphetamine 'binge and crash' decreases hydrogen sulfide and nitric oxide bioavailability. Plasma NO and $H_2S$ bioavailability are associated with endothelial and vascular dysfunction. Therefore, plasma and tissue metabolites of NO and $H_2S$ were measured at the end of the 4-week 'binge and crash' model of methamphetamine treatment. A significant reduction in sulfide metabolites-acid-labile and bound sulfane sulfur pools can be seen with methamphetamine compared to controls (FIGS. 1A and B). Similarly, NO metabolites—free nitrite and bound pool, S-nitrosothiol were decreased in methamphetamine treated group (FIGS. 1D and 1E). Methamphetamine causes a 3-fold reduction in plasma total sulfide (FIG. 1C) and a two-fold reduction in plasma total NO levels (FIG. 1F). Subsequently, in the skeletal muscle tissues a significant decrease in total sulfide levels were observed in mice treated with methamphetamine. Similarly, total NO in the skeletal muscles was significantly reduced in methamphetamine treated mice. These data evidence a role of $H_2S$ generation pathways (CSE, cystathionine beta synthase (CBS) or 3-MST) that can maintain the muscle tissue total sulfide levels in the methamphetamine treated mice. As mentioned above, CSE dependent $H_2S$ production regulates NO bioavailability under basal and ischemic states. This indicates that methamphetamine treatment significantly reduces $H_2S$ and NO metabolites, which is associated with endothelial dysfunction.

Methamphetamine 'binge and crash' blunts CSE expression and increases inflammation. $H_2S$ is predominantly produced by CSE and CBS enzymes in the vasculature and other tissues, whereas NO bioavailability is enzymatically influenced by eNOS. To check if compensation in sulfide levels was mediated by enzymatic mechanisms, the inventors measured the expressions of $H_2S$ producing enzymes, CSE and CBS in methamphetamine mice. Methamphetamine significantly decreased CSE gene expression (FIG. 2A), however, no significant changes were observed in gene expression of CBS in skeletal muscle tissue (FIG. 2B). Interestingly, no change in eNOS expression was observed, although there were decreased NO levels in methamphetamine treated mice (FIG. 2C). Posttranslational modifications such as phosphorylation of eNOS can influence the bioavailability of NO. So, the inventors further looked at the protein expressions of CSE, p-eNOS and total eNOS (FIG. 2D). Methamphetamine treated mice skeletal muscle showed decreased expressions of CSE and p-eNOS, quantified in FIGS. 2E and F; however, no change in total eNOS was observed.

Figure 3B:
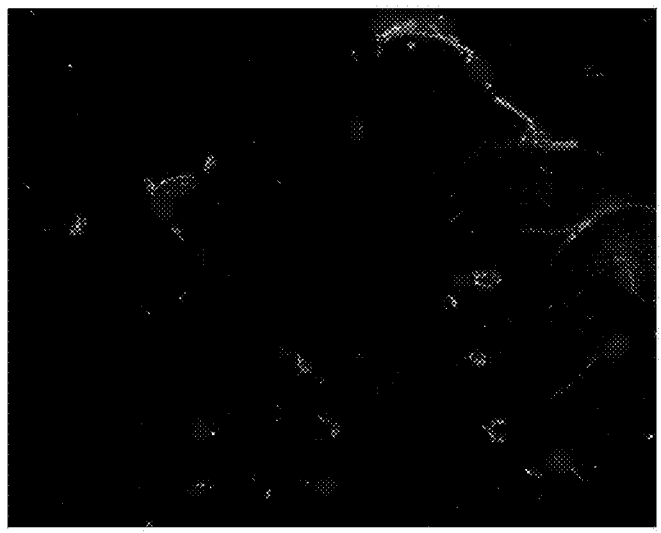
Figure 3C:
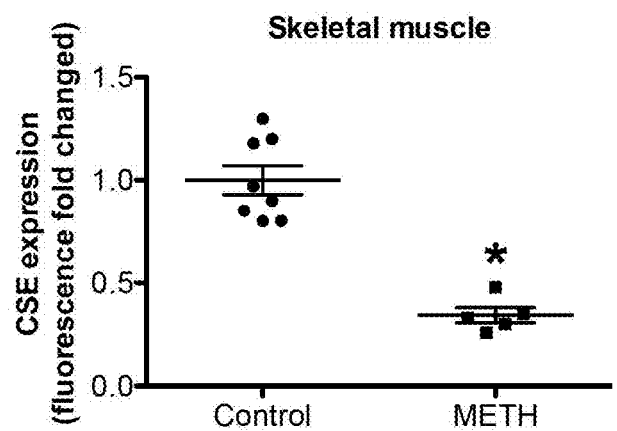
Figure 4B:
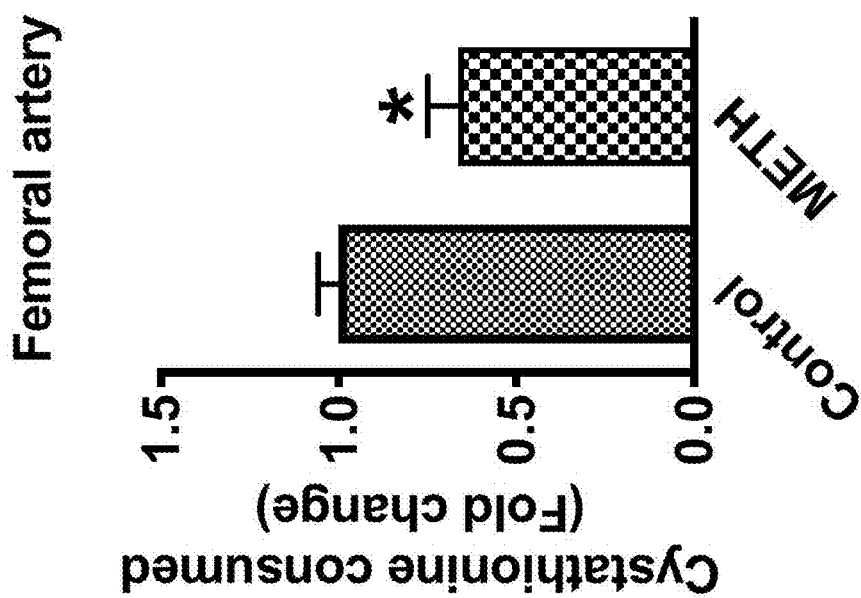
FIGS. 4A-4B show methamphetamine decreases CSE enzyme activity in mouse tissue.
Figure 4A:
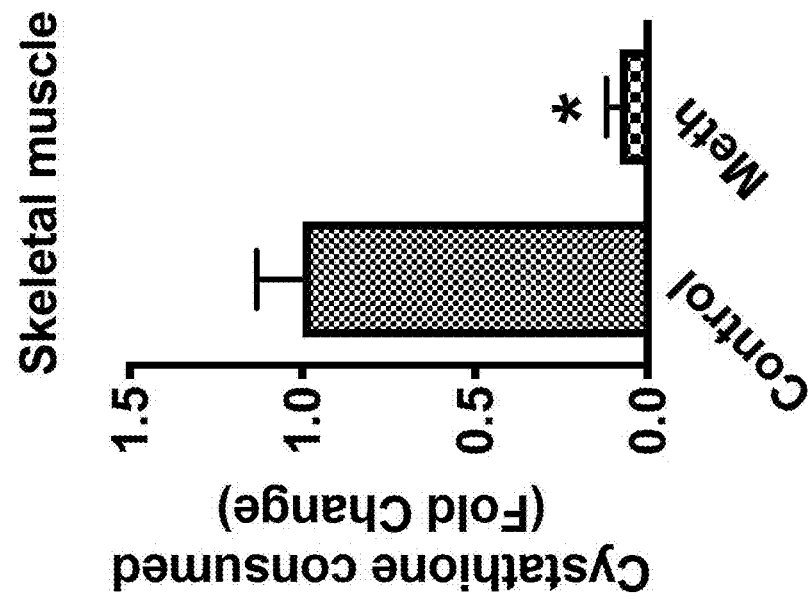
Figure 10A:
FIGS. 10A-10C show the effect of methamphetamine on CSE protein expression in humans.
Figure 10B:
Figure 10C:
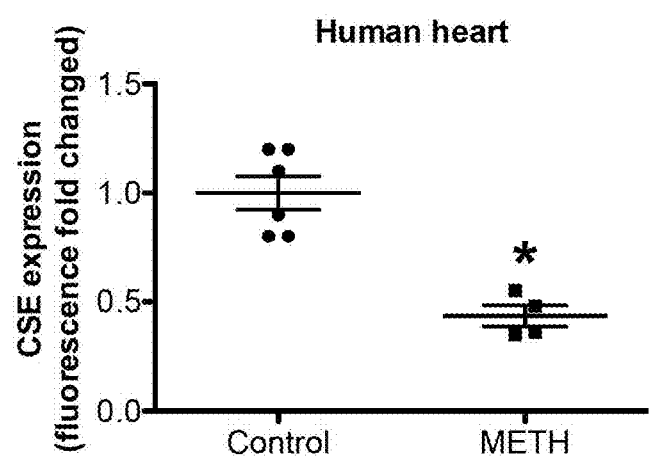

Methamphetamine blunts CSE expression in mouse and human tissues. Further to the inventors' observations of reduced CSE mRNA levels, the inventors examined CSE protein expression in sections of mouse skeletal muscle tissue from the 'binge and crash' model and human heart left ventricular (LV) tissues of methamphetamine users (FIGS. 3 and 10). The inventors found a significant decrease in vascular CSE expression in skeletal muscles of methamphetamine-treated mice compared to saline-treated controls (panels 3B vs 3A, respectively). Likewise, the inventors also found a significant reduction in vascular CSE expression (as seen by reduced co-localization with the endothelial marker CD31) in hearts collected post-mortem from human methamphetamine-users, compared to non-methamphetamine using individuals (panels 10B vs 10A, respectively). Semi-quantitative image analysis revealed that methamphetamine treatment in mice and methamphetamine use in humans significantly decreases CSE protein expression (panels 3C and 10C, respectively).

Figure 5C:
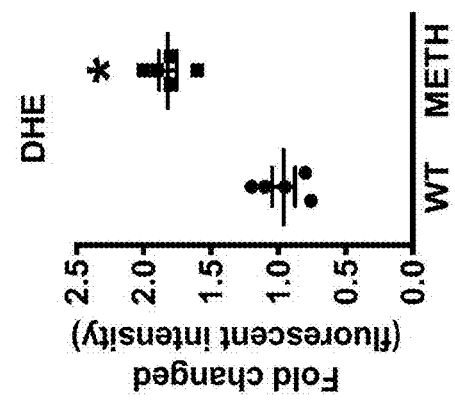
FIGS. 5A-5F show methamphetamine increases oxidative stress and inflammation in mouse skeletal muscle.
Figures 5A, 5B:
Figure 5D:
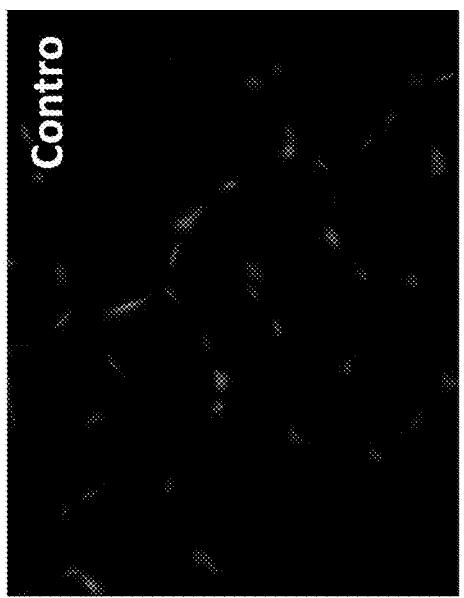
Figure 5E:
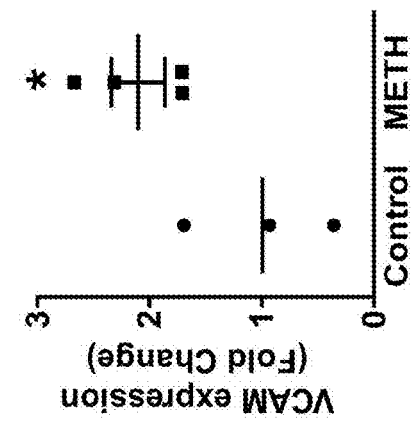
Figure 5F:
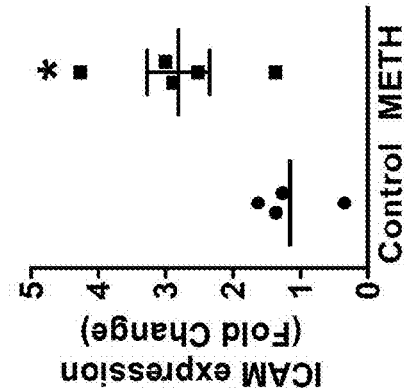

Methamphetamine 'binge and crash' increases skeletal tissue oxidative stress. FIG. 5 shows methamphetamine-mediated increase in oxidative stress using the fluorescent probe for superoxide, dihydrohydroethidine (DHE) in stained sections of skeletal muscle tissues treated with saline or methamphetamine, respectively. There is a significant increase in DHE fluorescence indicating an increase in oxidative stress production with methamphetamine treatments (FIGS. 5A and 5B). Chronic methamphetamine use can induce neuro- and cardio toxicity due to increased oxidative stress and pro-inflammatory cytokines including ICAM-1, VCAM-1, TNF-α, and IFN-γ expression that promotes atherosclerosis. $H_2S$ counteracts oxidative stress under chronic conditions through upregulation of antioxidant defenses. It also inhibits leukocyte-endothelial cell interactions in response to acute ischemia/reperfusion injury indicating anti-inflammatory action preventing endothelial cell activation. A concomitant increase in vascular cell adhesion molecule (VCAM-1) and intercellular adhesion molecule (ICAM-1) expression is observed with methamphetamine treatment (panels 5D and 5E). NADPH oxidases (NOX) are major sources of oxidative stress. NOx4 has a predominant role in regulating oxidative stress under ischemic stress conditions and in the cardiovascular system, the inventors observed a marginal increase in NOx4 expression with methamphetamine treatment in skeletal muscles (FIG. 5F). This indicates that increased oxidative stress and pro-inflammatory phenotype can contribute to alterations of vascular tone and blood flow.

Figure 11B:
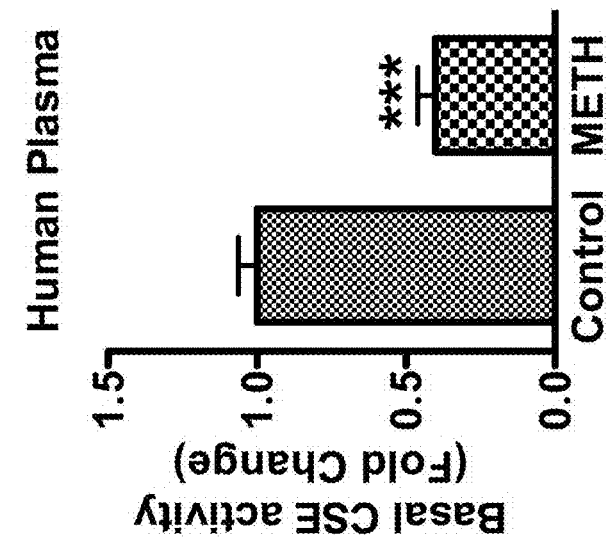
FIGS. 11A and 11B show methamphetamine decreases CSE activity in human plasma and endothelial cells.
Figure 11A:
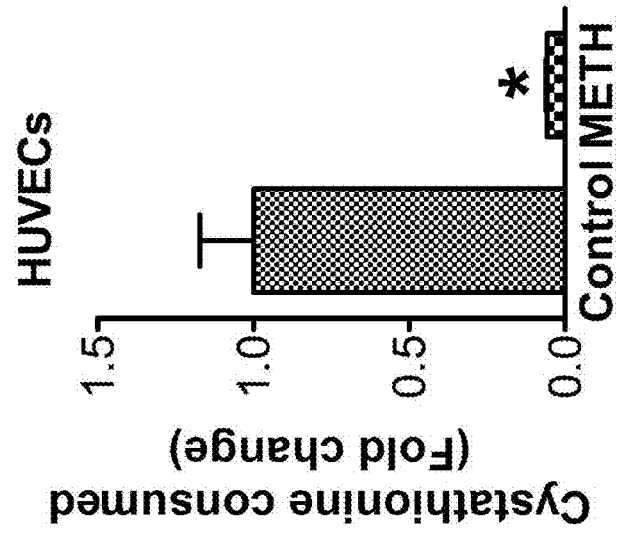

Methamphetamine 'binge and crash' decreases skeletal tissue CSE protein and endothelial CSE enzyme activity. Next, the inventors examined the effect of methamphetamine treatment (100 µM) on CSE enzyme activity in endothelial cells, which are a major component of vascular blood vessels, the inventors found that methamphetamine treatment of HUVECs treated for 30 min substantially decreased CSE enzyme activity over time compared to PBS control treatment (FIG. 11A). Apart from the MAECs, significant decrease in CSE activity was observed in skeletal muscle tissues of methamphetamine treated mice (FIG. 4A), and plasma from human methamphetamine-users compared to non-users (FIG. 11B).

Figure 7A:
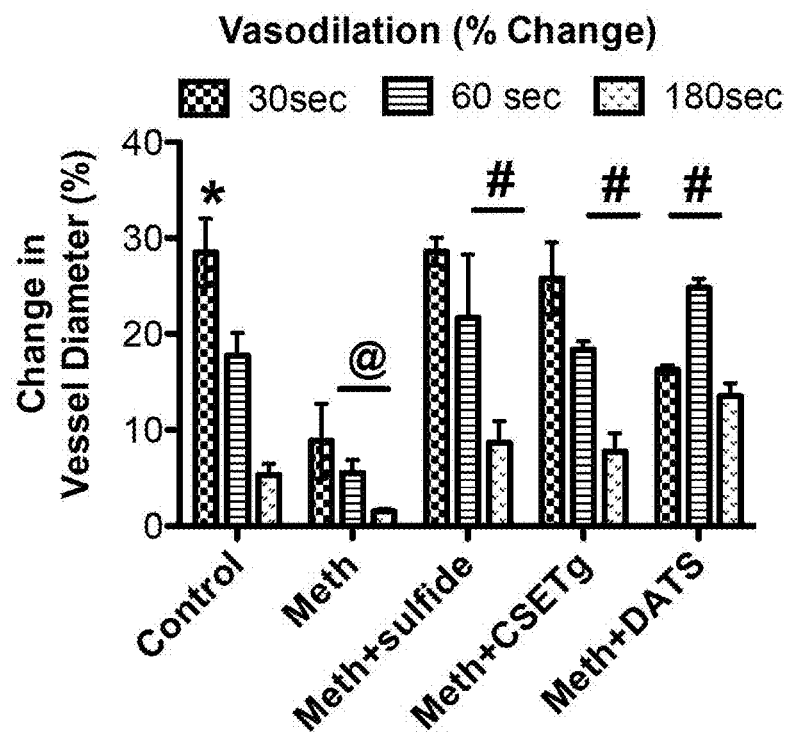
FIGS. 7A and 7B show exogenous sulfide/CSE expression rescues methamphetamine-mediated vascular dysfunction in mice.
Figure 7B:
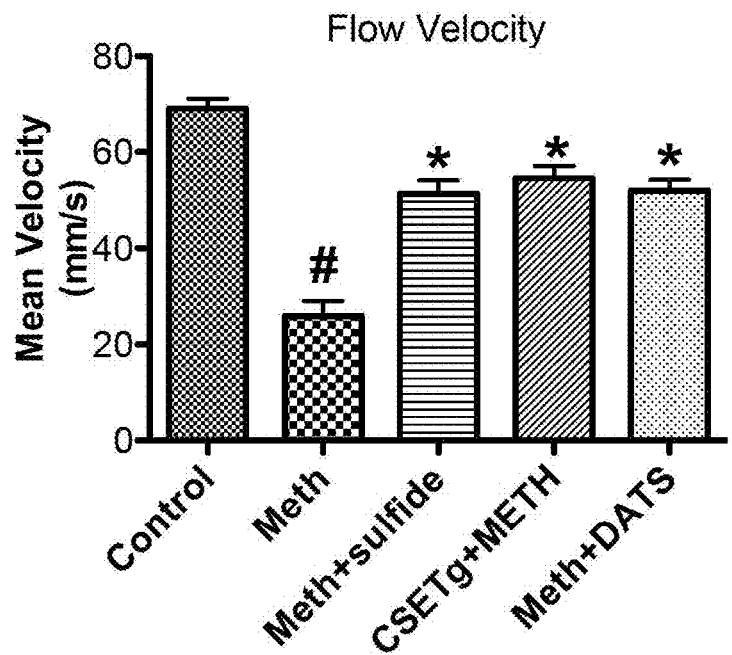
Figure 8A:
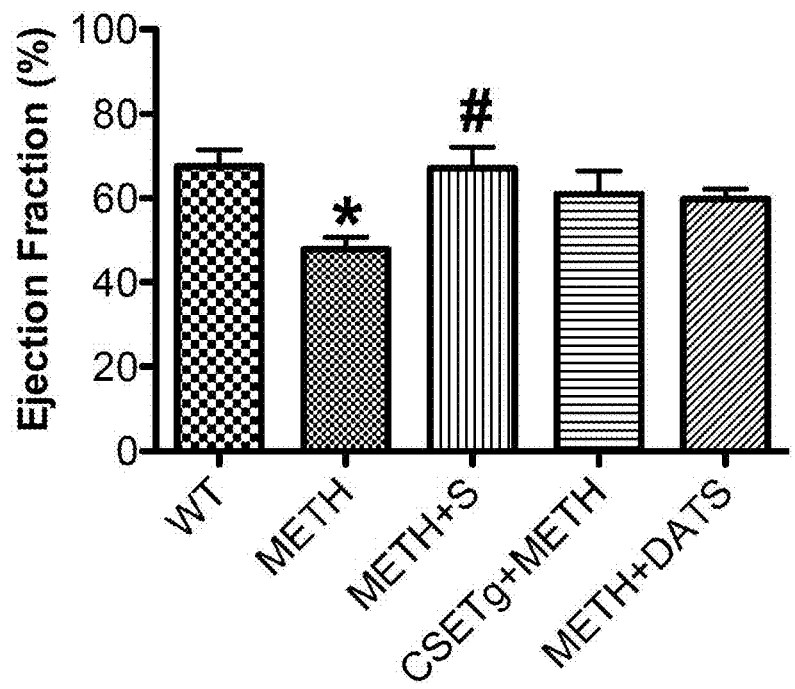
FIGS. 8A and 8B show exogenous sulfide/CSE rescues methamphetamine mediated cardiac dysfunction.
Figure 8B:
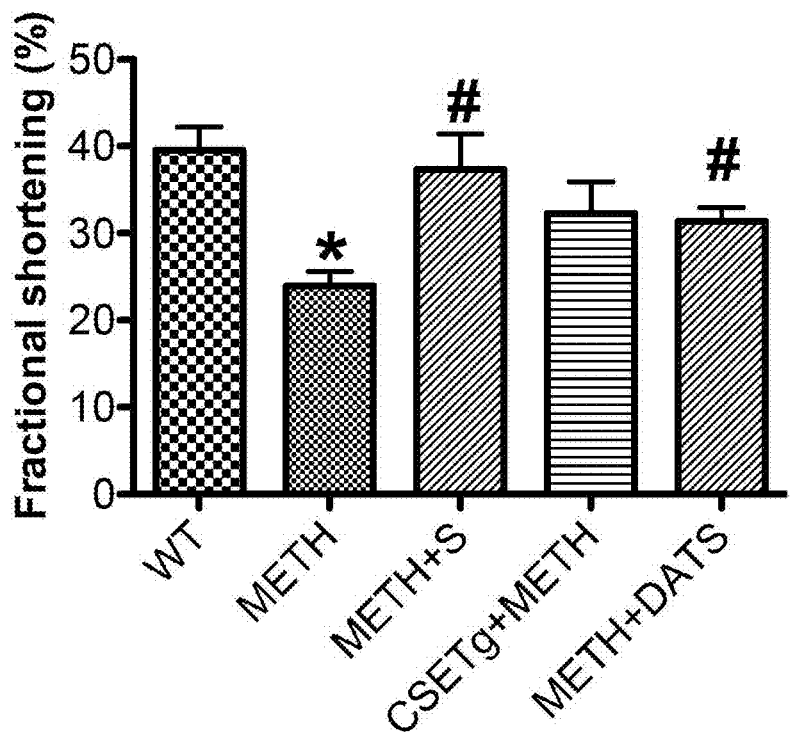
Figure 9A:
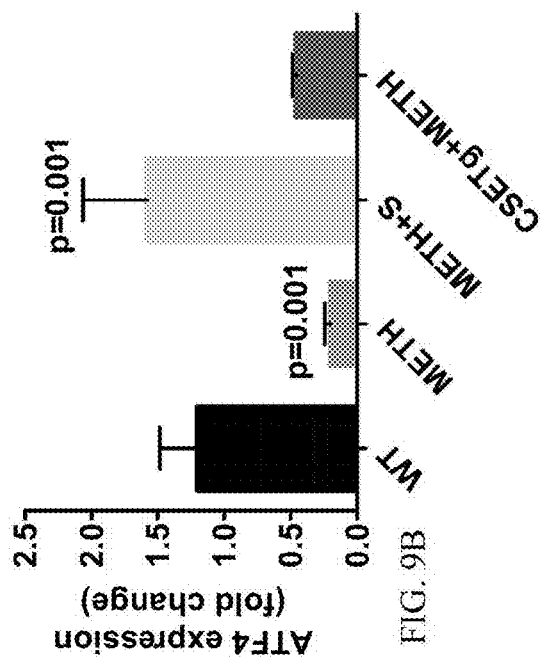
FIGS. 9A-9D show sulfide or CSE expression corrects methamphetamine defects in tissue aging genes.
Figure 9B:
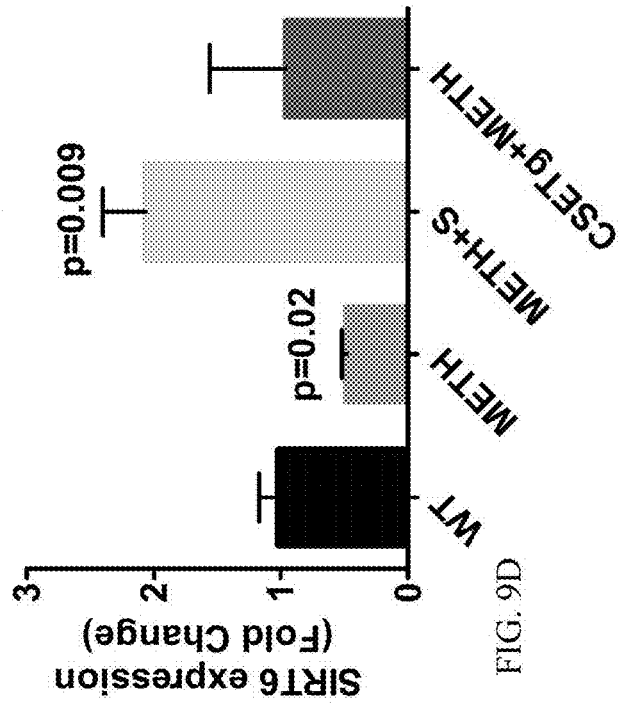
Figure 9C:
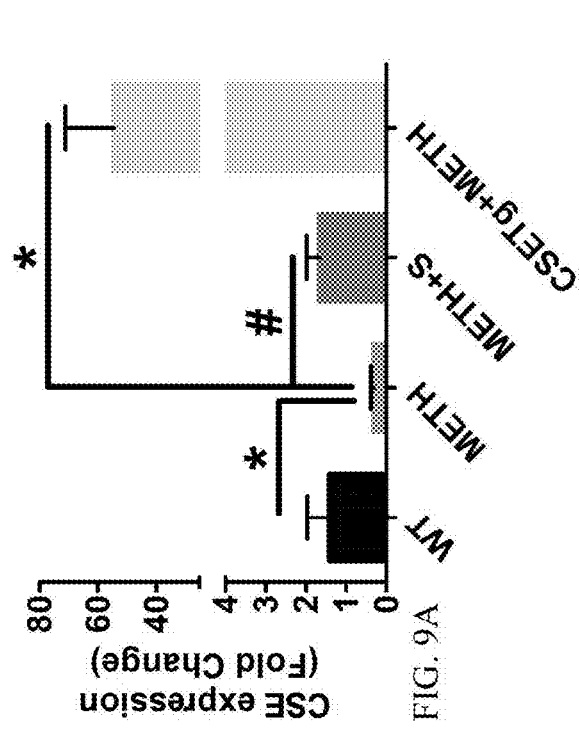
Figure 9D:
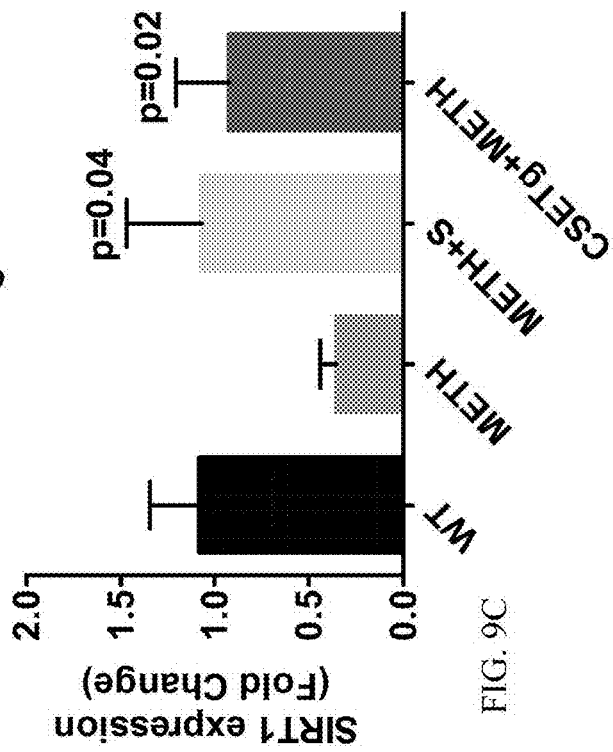

CSE or exogenous sulfide rescues methamphetamine inhibited vascular dilation via sulfide. To check whether rescue of vascular function can be rectified via upregulating CSE or sulfide bioavailability, the inventors used WT mice with parallel treatments of sulfide or CSE Tg mice along with methamphetamine treatments. the inventors observed a significant recovery in endothelial function via femoral vasodilation with FMD model via sulfide therapy or CSE overexpression (FIG. 7A). A significant recovery (25 and 30% respectively) was observed in mean flow velocity in methamphetamine treated mice with simultaneous sulfide therapy or in CSE Tg mice, as shown in FIG. 7B. Additionally, the inventors observed an increase in plasma total sulfide levels and three-fold increase in skeletal muscle tissues compared to both methamphetamine treated and control mice (results not shown). To check whether this therapy has any effect on CSE expression in vascular system, the inventors observed a two-fold increase in CSE activity in femoral arteries. This evidences that each of sulfide therapy and CSE overexpression rescues vascular function.

CSE Sulfide corrects pro-aging effects of methamphetamine: Aging is an independent predictor of cardiovascular complications. Advancing age promotes cardiovascular disease (CVD), ultimately leading to death. Aging and subsequent complications includes artery stiffening and endothelial dysfunction, which are responsible for the development of CVD. A previous study indicates that transcription factor, ATF4, can induce CSE expression. So, the inventors checked for changes in age-related genes, Sirtuins (Sirt), including ATF4 and CSE in tissues of methamphetamine treated mice. A significant increase in CSE and ATF4 expressions (FIGS. 9A and 9B, respectively) were observed with sulfide therapy and CSETg mice with methamphetamine treatments. Similarly, a minimum of a two-fold increase in expressions of Sirt1 and Sirt6 (FIGS. 9C and 9D, respectively) were also observed, compared to methamphetamine alone treated controls. This is evidence that the pro-aging effects of methamphetamine could partially be protected with exogenous sulfide or overexpression of CSE.

Discussion: Understanding of methamphetamine-related cardiovascular implications and the underlying molecular mechanisms remain poorly understood in current technology. Methamphetamine can have potentially fatal effects on cardiovascular pathology including atherosclerosis, which is characterized by plaque formation and occlusion of the blood vessels leading to increased morbidity and mortality. The development of occlusions in peripheral arteries in a young methamphetamine use subject are evidence of fatal effects of methamphetamine-mediated vascular pathology.

Decreased cerebral blood flow is observed through sustained methamphetamine-induced vasoconstriction of pial arterioles. Endothelial dysfunction is the primary cause for much cardiovascular pathology. Methamphetamine can cause severe endothelial dysfunction leading to increased atherosclerosis. In this disclosure, the inventors demonstrate methamphetamine mediated endovascular dysfunction and the underlying molecular mechanisms that regulate them. Results from FMD show that methamphetamine induces constriction in the femoral artery and decreases the mean blood velocity, resulting in dysfunctional vascular tone and defective blood flow. The gasotransmitters NO and $H_2S$ play key regulatory roles in many pathophysiological functions. Both NO—$H_2S$ signaling pathway crosstalk to mediate their effects on vascular functions, including vasodilation and vascular remodeling. the inventors' results indicate that defect in vasodilation is associated with significant reduction $H_2S$ and NO bioavailability in plasmas from methamphetamine-treated mice. To further check if these changes in circulation were reflected in the tissues, the inventors checked the sulfide and NO levels in the skeletal muscle tissues. the inventors observed no significant changes in total sulfide levels, however, total NO levels were significantly decreased compared to the saline controls. $H_2S$ regulates NO metabolic pathways during ischemic vascular remodeling, which is reflected in patients with clinical vascular disease. Similar to these observations, the inventors saw a decrease in acid-labile sulfide levels in human plasma samples from methamphetamine-users compared to age matched healthy controls, however, there is a trend of decreasing total NO levels with no statistical significance.

Cystathionine γ-lyase (CSE) is a major enzyme producing $H_2S$ in the vascular system that plays critical roles in endothelial function and cardiovascular health. However, $H_2S$ can also be synthesized by CBS, another enzyme in the transsulfuration pathway. CSE dependent $H_2S$ production is critically important for regulation of vascular function and remodeling. Compensation of $H_2S$ bioavailability in the skeletal muscle can be possible via increased CBS expression. Interestingly, CSE gene and protein expressions were significantly reduced with methamphetamine treatment in skeletal muscle tissues (4A and D). No statistically significant compensation was observed in CBS or changes in total eNOS expression, though this may have been due to the small sample size. It is noteworthy to see a decrease in eNOS phosphorylation at Ser1177, in skeletal muscle tissues of methamphetamine-treated mice compared to saline controls. This evidences that methamphetamine significantly inhibits CSE and p-eNOS expressions thereby decreasing $H_2S$ and NO bioavailability in mice. Likewise, immunohistology of skeletal muscle tissues shows a decrease in CSE expression in methamphetamine tissue compared to saline controls. Similarly, a significant decrease in CSE activity was observed in endothelial cells and skeletal muscle of mice treated with methamphetamine. Corroborating these observations, LV heart sections from humans revealed that methamphetamine users have a significant reduction in CSE compared to non-methamphetamine controls. This corresponds with the decrease in CSE activity in methamphetamine-treated endothelial cells, mouse skeletal muscle tissues and in plasma of human methamphetamine-users. These results evidence that methamphetamine treatment can critically inhibit CSE expression and subsequent $H_2S$ bioavailability.

Methamphetamine can induce oxidative stress and ROS production that can lead to long-lasting damage to neurological system. Enhanced oxidative stress represent common effects of methamphetamine use; specific reasons for these molecular changes underlying much of the cardiovascular complications are still not known completely. Methamphetamine-mediated increase in oxidative stress using the fluorescent probe for superoxide, dihydrohydroethidine (DHE) in stained sections of skeletal muscle tissues of mice treated with saline or methamphetamine, respectively. There was a significant increase in DHE fluorescence indicating an increase in oxidative stress production with methamphetamine treatments. These results substantiate the inventors' observations that methamphetamine increases oxidative stress and may lead to cardiovascular dysfunction. Cellular adhesion molecules, VCAM-1 and ICAM-1 play important roles in transendothelial migration of leukocytes, and within the milieu of the atherosclerotic plaque. Circulating ICAM-1, VCAM-1 have been detected in plasma and are elevated during inflammatory conditions in the prediction of cardiovascular disease. Chronic methamphetamine use can induce neuro- and cardio-toxicity due to increased oxidative stress and pro-inflammatory cytokines including ICAM-1, VCAM-1, TNF-α, and IFN-γ expression that promotes atherosclerosis. $H_2S$ counteracts oxidative stress under chronic conditions through upregulation of antioxidant defenses. It has also been shown to inhibit leukocyte-endothelial cell interactions in response to acute ischemia/reperfusion injury indicating anti-inflammatory action preventing endothelial cell activation. The inventors showed that methamphetamine significantly decreased CSE but not CBS gene expression in skeletal muscle tissue. Importantly, a concomitant increase in ICAM-1 and VCAM-1 expression is observed with methamphetamine treatment. NADPH oxidases (NOX) are major sources of oxidative stress. Nox4 has a predominant role in regulating oxidative stress under ischemic stress conditions and in the cardiovascular system. Furthermore, recent literature implicates a role for NOX in methamphetamine-induced oxidative stress in brain endothelial cells. However, the role of Nox4 in methamphetamine-induced oxidative stress and regulation of vasomotor activity in the vasculature requires further investigation. A trend of increasing NOX4 gene expression can be observed in skeletal muscle tissues of methamphetamine-treated mice. These data reveal that loss of CSE gene expression is associated with increased pro-inflammatory activation in the vasculature.

Defects in CSE and $H_2S$ critically impair vascular function, including vasodilation and vessel remodeling. Results from FMD indicate a dysfunctional vascular tone, femoral artery constriction and decreased blood flow due to methamphetamine-mediated CSE/$H_2S$ inhibition. Severe impairment of CSE/$H_2S$ leads to significant reduction in plasma and tissue NO levels and tissue growth factor expression resulting in impaired revascularization and blood flow responses, which can be rectified by exogenous $H_2S$ based donor therapy. the inventors increased the CSE/$H_2S$ levels through exogenous or endogenous delivery to rectify methamphetamine-mediated vascular defects, via simultaneous treatments of methamphetamine and exogenous treatment with $Na_2S$ in C57BL6/J mice or in CSE Tg mice. FMD analyses of these mice groups showed a significant recovery in the vessel dilation and blood flow velocities, which is associated with concurrent elevation of $H_2S$ bioavailability in plasma and skeletal muscle and blood vessel CSE activity in femoral arteries. This further corroborates the inventors' observations that endogenous CSE/$H_2S$ regulates endothelial and vascular function and rescues methamphetamine-inhibited vascular tone.

In the current disclosure the inventors demonstrate that methamphetamine induces endothelial dysfunction via CSE inhibition and subsequent reduction of $H_2S$ bioavailability. the inventors' results reveal for the first time that a methamphetamine mediated decrease in CSE expression and activity can contribute to vascular dysfunction including increased oxidative stress, inflammatory activation, and reduced $H_2S$/NO bioavailability in mouse models. However, the inventors only observed a decrease in acid-labile sulfide pools in human methamphetamine-users. There could be many possibilities due to duration of the methamphetamine and how long the user had been off methamphetamine usage.

Methamphetamine use has effects on vascular dysfunction and on circulating metabolites of $H_2S$/NO that regulate critical functions of cardiovascular pathophysiology. the inventors' observations clearly demonstrated that methamphetamine severely dysregulates normal vascular tone of the femoral artery, which can be rectified by exogenous/endogenous CSE/$H_2S$ therapy. Collectively, the inventors' results reveal for the first time that methamphetamine inhibits CSE vascular expression and activity in endothelial cells that contribute to vascular dysfunction. Methamphetamine use leads to atherosclerosis and associated complications, thereby contribute to increased cardiovascular disease. the inventors' study has revealed important insights into methamphetamine-mediated vascular dysfunction and associated molecular signaling, highlighting clinical importance of CSE/$H_2S$ role, as a therapeutic targets.

Figure 12:
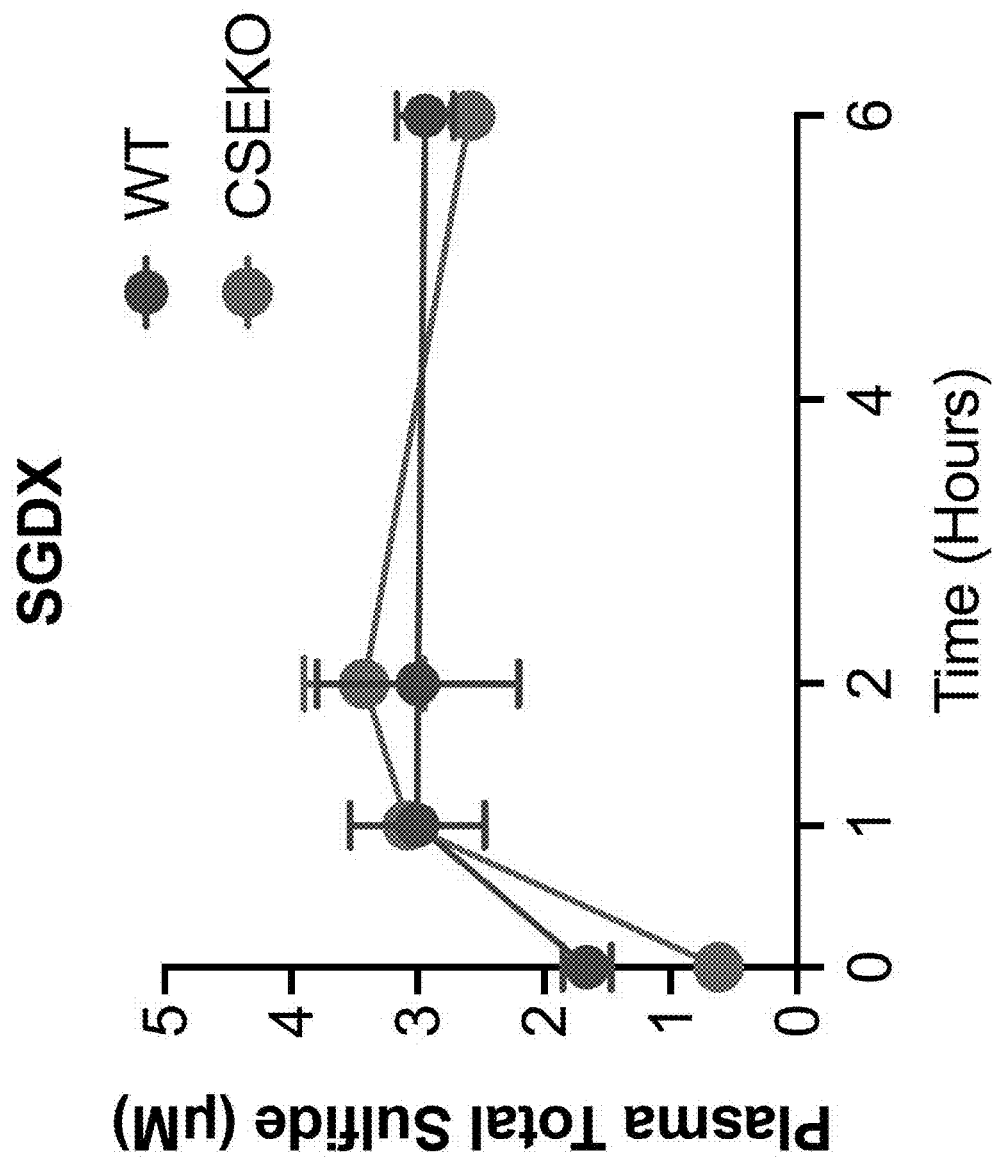
FIG. 12 shows sulfide release with Sugammadex in WT and CSEKO mice.
Figure 13C:
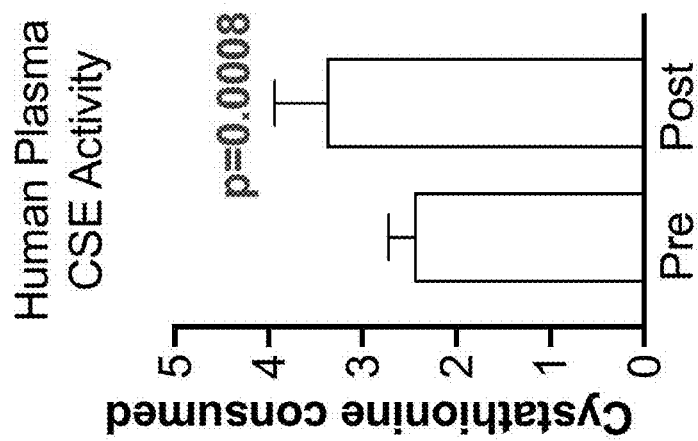
FIGS. 13A-13C show sulfide release and CSE activity with Sugammadex in Human Plasma.
Figure 13B:
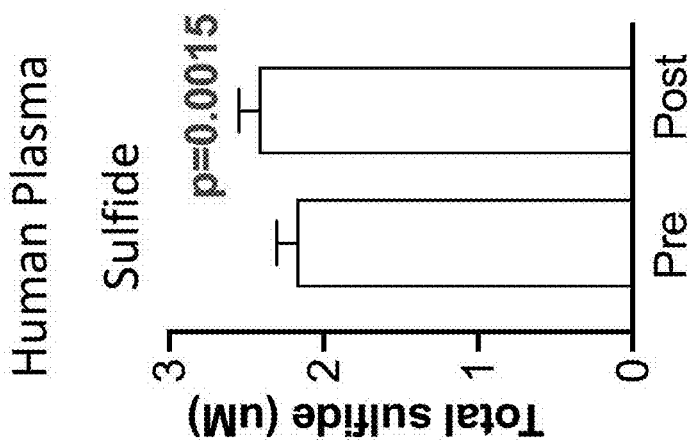
Figure 13A:
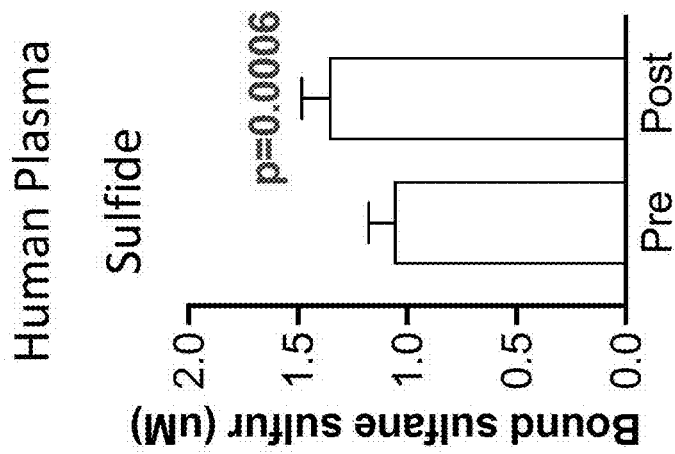

Turning to FIGS. 12-13C, experiments with the pharmaceutical Sugammadex is shown, monitoring sulfide levels in wild type and CSE knockout mice (FIG. 12) and demonstrating that it also increases human bound sulfane sulfur and total sulfide levels in human blood (FIGS. 13A and 13B) along with increased plasma CSE activity (FIG. 13C).

Sugammadex is a γ-cyclodextrin medication for the reversal of neuromuscular blockade induced by rocuronium and vecuronium in general anesthesia. It has a molecular formula of $C_{72}H_{104}Na_8O_{48}S_8$, and a chemical structure of.

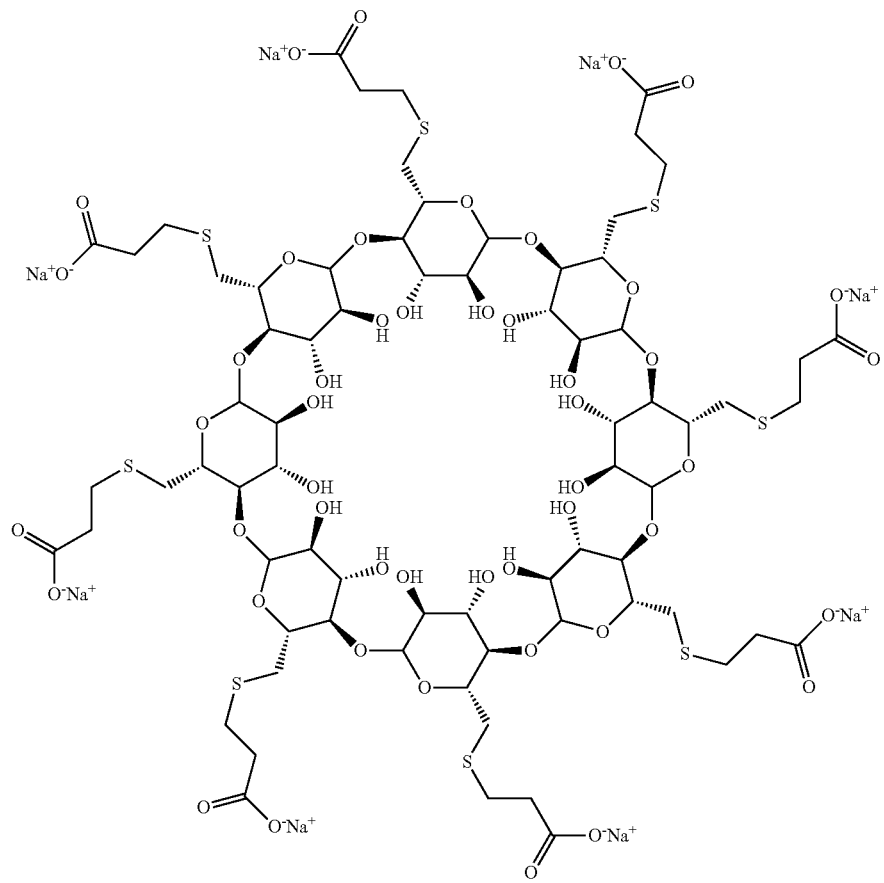

In clinical practice, sugammadex is administered at a dose of 4 mg/kg to up to 16 mg/kg for its current use. In the inventors' mice studies, the inventors used a single injection of 0.2 mg/kg for pharmacokinetic studies, which was a 20 to 80 times lower than the clinical usage of sugammadex.

For initial experiments disclosed herein, Sulfide and DATS concentrations in drinking water were used at 30 uM at an average of 3-4 mls of water intake. The inventors have previously used sulfide and DATS intravenously at 200 ug/kg concentration twice daily in mice with chronic ischemia.

Pharmaceutical Compositions: The methods described herein can also include the administrations of pharmaceutically acceptable compositions that include the therapeutic, or a pharmaceutically acceptable salt, solvate, or prodrug thereof. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, $22^{nd}$ Ed., Gennaro, Ed., Lippencott Williams & Wilkins (2012), a well-known reference text in this field, and in the USP/NF (United States Pharmacopeia and the National Formulary), each of which is incorporated by reference. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients, 8th* Edition, Sheskey et al., Eds., Pharmaceutical Press (2017), which is incorporated by reference.

The methods described herein can include the administration of a therapeutic, or prodrugs or pharmaceutical compositions thereof, or other therapeutic agents.

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration: The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion-controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerin.

Coatings: The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Parenteral Administration: Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 μm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g., poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery: Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences*, 81(1): 1-10, 1992).

Oral transmucosal absorption is generally rapid because of the rich vascular supply to the mucosa and allows for a rapid rise in blood concentrations of the therapeutic.

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art (see, e.g., Biesalski, U.S. Pat. No. 5,112,598, and Biesalski, U.S. Pat. No. 5,556,611).

Formulations for sublingual administration can also be used, including powders and aerosol formulations. Exemplary formulations include rapidly disintegrating tablets and liquid-filled soft gelatin capsules.

The pharmaceutical compositions of the invention may be dispensed to the subject under treatment with the help of an applicator. The applicator to be used may depend on the specific medical condition being treated, amount and physical status of the pharmaceutical composition, and choice of those skilled in the art. Conventional pharmaceutical carriers, aqueous, powder or oily bases, thickeners and the like may be employed. In certain applications, an ointment, lotion, cream, gel or similar formulation can be provided that can be applied to the skin using the fingers. Such formulations are typically provided in a squeeze tube or bottle or a pot, or in a roll-on, wherein a ball is secured in the top of a container of the formulation, wherein the ball is permitted to roll. By rolling the ball over the skin surface, liquid in the container is transferred to the skin in a controlled manner. An alternative delivery mechanism includes a container with a perforated lid with a mechanism for advancing an extrudable formulation through the lid. In another form, a gel formulation with sufficient structural integrity to maintain its shape is provided, which is advanced up a tube and applied to the skin (e.g., in a stick form). An advantage of the stick form is that only the formulation contacts the skin in the application process, not the fingers or a portion of a container. A liquid or gel can also be placed using an applicator, e.g., a wand, a sponge, a syringe, or other suitable method.

The pharmaceutical compositions of the invention may be provided to the subject or the medical professional in charge of dispensing the composition to the subject, along with instructional material. The instructional material includes a publication, a recording, a diagram, or any other medium of expression, which may be used to communicate the usefulness of the composition and/or compound used in the practice of the invention in a kit. The instructional material of the kit may, for example, be affixed to a container that contains the compound and/or composition used in the practice of the invention or shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Other routes of administration to the affected area which are contemplated include: transdermal, mucosal, rectal, and vaginal, or topical (for example, in a carrier vehicle, a topical control release patch, in a wound dressing, a hydrocolloid, a foam, or a hydrogel, a cream, a gel, a lotion, an ointment, a liquid crystal emulsion (LCE), and/or a microemulsion). An appropriate biological carrier or pharmaceutically acceptable excipient may be used. Compounds administered may, in various embodiments, be racemic, isomerically purified, or isomerically pure.

Transmucosal Administration: Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, a non-aerosol liquid formulation, or a dry powder, placed within or near the rectum ("transrectal" formulations), or administered to the urethra as a suppository, ointment, or the like. Application in the oral or nasal cavities are options for high absorption that does not make a first pass in the liver.

Transrectal Administration: Transrectal dosage forms may include rectal suppositories, creams, ointments, and liquid formulations (enemas). The suppository, cream, ointment, or liquid formulation for transrectal delivery comprises a therapeutically effective amount of the selected active agent and one or more conventional nontoxic carriers suitable for transrectal drug administration. The transrectal dosage forms of the present invention may be manufactured using conventional processes. The transrectal dosage unit may be fabricated to disintegrate rapidly or over a period of several hours. The time period for complete disintegration may be in the range of from about 10 minutes to about 6 hours, e.g., less than about 3 hours. This can be an option for administration for high absorption that does not make a first pass in the liver.

Vaginal or Perivaginal Administration. Vaginal or perivaginal dosage forms may include vaginal suppositories, creams, ointments, liquid formulations, pessaries, tampons, gels, pastes, foams, or sprays. The suppository, cream, ointment, liquid formulation, pessary, tampon, gel, paste, foam, or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours. This can be an option for administration for high absorption that does not make a first pass in the liver.

Topical Formulations: Topical formulations may be in any form suitable for application to the body surface, and may comprise, for example, an ointment, cream, gel, lotion, solution, paste or the like, and/or may be prepared so as to contain liposomes, micelles, and/or microspheres. In certain embodiments, topical formulations herein are ointments, creams, and gels.

Transdermal Administration: Transdermal compound administration, which is known to one skilled in the art, involves the delivery of pharmaceutical compounds via percutaneous passage of the compound into the systemic circulation of the patient. Topical administration may also involve the use of transdermal administration such as transdermal patches or iontophoresis devices. Other components may be incorporated into the transdermal patches as well. For example, compositions and/or transdermal patches may be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions may include creams, sprays, lotions, gels, ointments, eye drops, nose drops, ear drops, and the like. In such dosage forms, the compositions of the invention may be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water, and sorbitol solution. In addition, the compositions may contain polyethylene glycol 400. They may be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, may be impregnated with the compositions in solution, lotion, cream, ointment, or other such form may also be used for topical application. The compositions may also be applied topically using a transdermal system, such as one of an acrylic-based polymer adhesive with a resinous crosslinking agent impregnated with the composition and laminated to an impermeable backing.

Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir that, in this case, may be either a polymeric matrix as described above, or be a liquid or hydrogel reservoir, or take some other form.

Additional Administration Forms. Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Application Nos. 20030147952, 20030104062, 20030104053, 20030044466, 20030039688, and 20020051820. Additional dosage forms of this invention also include dosage forms as described in PCT Application Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757, such forms incorporated by reference.

Solutions: After an $H_2S$ donor has been selected, it may be dissolved into a solution. The solution may be an aqueous-based solution, such as water, saline, or the like. In some variations, other fluids and solutions may be appropriate.

Various formulations of saline are known in the art and may be used with the present invention. For example, the saline may be lactated Ringer's solution, acetated Ringer's solution, phosphate buffered saline (PBS), Dulbecco's phosphate buffered saline (D-PBS), Tris-buffered saline (TBS), Hank's balanced salt solution (HBSS), or Standard saline citrate (SSC).

The saline solutions of the present invention are, in certain embodiments, "normal saline" (i.e., a solution of about 0.9% w/v of NaCl). Normal saline has a slightly higher degree of osmolality compared to blood; however, in various embodiments, the saline may be isotonic in the body of a subject such as a human patient. In certain embodiments, "half-normal saline" (i.e., about 0.45% NaCl) or "quarter-normal saline" (i.e., about 0.22% NaCl) may be used with the present invention. Optionally, about 5% dextrose or about 4.5 g/dL of glucose may be included in the saline. In various embodiments, one or more salt, buffer, amino acid and/or antimicrobial agent may be included in the saline.

In various embodiments, a preservative or stabilizer may be included in the composition or solution. For example, the prevention of the action of microorganisms may be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal, or combinations thereof. Agents that may be included suitable for use include sterile aqueous solutions or dispersions and sterile powders for the extemporaneous preparation of sterile solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, and the like. Appropriate stabilizers or preservatives may be selected according to the route of administration desired. A particle filter or microbe filter may be used and may be necessary according to the route of administration desired.

The weight ranges of compounds in the solution may vary. For example, in various embodiments, the composition may comprise about 0.1-10 wt %, more preferably 1-5 wt % $H_2S$ donor, about 1-5 wt % preservative/stabilizer, about 1-5 wt % NaCl, and about 85%-97% water. The ratio of $H_2S$ donor to water may be varied as needed to achieve the desired treatment of the endothelial dysfunction condition.

The solution and/or composition may also be sterilized prior to administration. Methods for sterilization are well known in the art and include heating, boiling, pressurizing, filtering, exposure to a sanitizing chemical (for example, chlorination followed by dechlorination or removal of chlorine from solution), aeration, autoclaving, and the like.

The $H_2S$ donor may be formulated into a solution in any number of ways. For example, it may be solubilized by agitation or by sonication, or other methods known in the art. After the $H_2S$ donor has been solubilized, it may be administered to a subject in need of treatment of an endothelial dysfunction condition. In certain embodiments, an $H_2S$ donor is admixed with a solution in a closed vacuum container, and the combined solutions are then mechanically agitated for 3-5 minutes and held in a thermo-neutral sonicator until use.

In certain embodiments, solutions of the present invention may be a component of an emulsion, such as a water-in-oil or an oil-in-water emulsion, including a lipid emulsion, such as a soybean oil emulsion. Certain emulsions have been described previously for intravenous (da Silva Telles, et al., 2004, Rev. Bras. Anaestesiol Campianas 54(5):2004) or epidural administration (Chai et al. 2008, British J Anesthesia 100:109-115), such described emulsion techniques incorporated by reference herein.

Pharmaceutical compositions of the present invention comprise an effective amount of one or more $H_2S$ donors dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one $H_2S$ donor in solution or additional active ingredient will be known to those of skill in the art in light of the present disclosure, as exemplified by "Remington: The Science and Practice of Pharmacy," 20th Edition (2000), which is incorporated herein by reference in its entirety. Moreover, for animal (for example, human) administration, it will be understood that preparations should meet sterility, pyrogenicity, general safety and purity standards as required by FDA Office of Biological Standards.

In various embodiments, the compositions of the present invention further comprise cyclodextrin. Cyclodextrins are a general class of molecules composed of glucose units connected to form a series of oligosaccharide rings (See Challa et al., 2005, AAPS PharmSciTech 6:E329-E357). In nature, the enzymatic digestion of starch by cyclodextrin glycosyltransferase (CGTase) produces a mixture of cyclodextrins comprised of 6, 7 and 8 anhydroglucose units in the ring structure (α-, β-, and γ-cyclodextrin, respectively). Commercially, cyclodextrins are also produced from starch, but different, more specific enzymes are used. Cyclodextrins have been employed in formulations to facilitate the delivery of cisapride, chloramphenicol, dexamethasone, dextromethorphan, diphenhydramine, hydrocortisone, itraconazole, and nitroglycerin (Welliver and McDonough, 2007, Sci World J, 7:364-371). In various embodiments, the cyclodextrin of the invention is hydroxypropyl-Beta-cyclodextrin, sulfobutylether-beta-cyclodextrin, alpha-dextrin or combinations thereof. In certain embodiments, cyclodextrin may be used as a solubilizing agent.

In various other embodiments, compositions of the present invention may comprise human serum albumin purified from plasma, or recombinant human serum albumin. In certain embodiments, human serum albumin may be used as a solubilizing agent. In other embodiments, the compositions of the invention may comprise propylene glycol. In other embodiments, the compositions of the invention may comprise perfluorooctyl bromide. In other embodiments, the compositions of the invention may comprise perfluorocarbon. In certain embodiments, perfluorocarbon may be used as a solubilizing agent.

In various embodiments, a preservative or stabilizer may be included in the composition or solution. For example, the prevention of the action of microorganisms may be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal, or combinations thereof. Agents which may be included suitable for use include sterile aqueous solutions or dispersions and sterile powders for the extemporaneous preparation of sterile solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, etc. Appropriate stabilizers or preservatives may be selected according to the route of administration desired. A particle filter or microbe filter may be used and may be necessary according to the route of administration desired.

Administration of the disclosed compositions in a method of treatment may be achieved in a number of different ways, using methods known in the art. Such methods include, but are not limited to, topically administering solutions, suspensions, creams, pastes, oils, lotions, gels, foam, hydrogel, ointment, liposomes, emulsions, liquid crystal emulsions, and nano-emulsions.

The therapeutic and prophylactic methods of the invention thus encompass the use of pharmaceutical compositions of the invention. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. For example, unit dose container may be such that an $H_2S$ donor solution is contained in a crushable sealed ampoule which in turn is enclosed in protective covering on which pressure is applied to crush the ampoule which then releases the $H_2S$ donor solution for percolation through a flint-type tip which capped the ampoule in protective covering. When such packaging configuration is employed, care is taken to leave as little as possible or ideally no headspace in ampoule for any volatile portion of the solution to escape and cause a change in solution composition over a period of shelf life.

Although the description of pharmaceutical compositions provided herein are principally directed to pharmaceutical compositions which are suitable for ethical administration to humans, it will be understood by the skilled artisan that such compositions are generally suitable for administration to animals of all sorts, including mammals. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, vaginal, topical, intranasal, buccal, or another route of administration.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Non-limiting examples of such an additional pharmaceutically active agents are fluorouracil cream, imiquimod cream, ingenol mebutate gel, diclofenac sodium gel, topical retinoids, and tirbanibulin (Klisyri) ointment.

Controlled- or sustained-release formulations of a pharmaceutical composition of the invention may be made using conventional technology.

Formulations of a pharmaceutical composition suitable for topical administration comprise the active ingredient combined with a pharmaceutically acceptable carrier, such as sterile water or sterile isotonic saline. Formulations may be prepared, packaged, or sold in unit dosage form, such as in ampules, crushable or otherwise, or in multi-dose containers containing a preservative. Formulations for topical administration include, but are not limited to, suspensions, solutions, emulsions in oily or aqueous vehicles, solutions, suspensions, creams, pastes, oils, lotions, gels, foam, hydrogel, ointment, liposomes, emulsions, liquid crystal emulsions, nanoemulsions, implantable sustained-release or biodegradable formulations. Such formulations may further comprise one or more additional ingredients including, but not limited to, suspending, stabilizing, or dispersing agents.

The pharmaceutical compositions may be prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile formulations may be prepared using a non-toxic acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other formulations that are useful include those which comprise the active ingredient in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

In some embodiments, the pharmaceutical compositions of the invention may be contained in a crushable ampule irrespective of the route of delivery to the patient.

It is contemplated that any embodiment discussed in this specification may be implemented with respect to any method or composition of the invention, and vice versa. Furthermore, compositions of the invention may be used to achieve methods of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

Dosing Regimes

The present methods for treating endothelial dysfunctions are carried out by administering a therapeutic for a time and in an amount sufficient to result in decreased endothelial dysfunction.

The amount and frequency of administration of the compositions can vary depending on, for example, what is being administered, the state of the patient, and the manner of administration. In therapeutic applications, compositions can be administered to a patient suffering from endothelial dysfunction in an amount sufficient to relieve or least partially relieve the symptoms of the endothelial dysfunction and its complications. The dosage is likely to depend on such variables as the type and extent of progression of the endothelial dysfunction, the severity of the endothelial dysfunction, the age, weight and general condition of the particular patient, the relative biological efficacy of the composition selected, formulation of the excipient, the route of administration, and the judgment of the attending clinician. Effective doses can be extrapolated from dose response curves derived from in vitro or animal model test system. An effective dose is a dose that produces a desirable clinical outcome by, for example, improving a sign or symptom of the endothelial dysfunction or slowing its progression.

The amount of therapeutic per dose can vary. For example, a subject can receive from about 0.1 µg/kg to about 10,000 µg/kg. Generally, the therapeutic is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of therapeutic (e.g., 0.089-3.9 mmol) or 0.1-50 µmol of therapeutic (e.g., 0.1-µmol or 0.4-20 µmol).

The plasma concentration of therapeutic can also be measured according to methods known in the art. Exemplary peak plasma concentrations of therapeutic can range from 0.05-10 µM, 0.1-10 µM, 0.1-5.0 µM, or 0.1-1 µM. Alternatively, the average plasma levels of therapeutic can range from 400-1200 µM (e.g., between 500-1000 µM) or between 50-250 µM (e.g., between 40-200 µM). In some embodiments where sustained release of the drug is desirable, the peak plasma concentrations (e.g., of therapeutic) may be maintained for 6-14 hours, e.g., for 6-12 or 6-10 hours. In other embodiments where immediate release of the drug is desirable, the peak plasma concentration (e.g., of therapeutic) may be maintained for, e.g., 30 minutes.

The frequency of treatment may also vary. The subject can be treated one or more times per day with therapeutic (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits: Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce symptoms and/or underlying cause of the endothelial dysfunction.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. The present disclosure also contemplates other embodiments "comprising," "consisting of" and "consisting essentially of," the embodiments or elements presented herein, whether explicitly set forth or not. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items, while only the terms "consisting of" and "consisting only of" are to be construed in the limitative sense.

We claim:

1. A method of treating or preventing methamphetamine related endothelial dysfunction in a patient comprising:
    administering to the patient an effective dose of a pharmacologic composition;
    the composition comprising a therapeutic;
    the therapeutic including a hydrogen sulfide ($H_2S$) donor, or a salt, solvate, ester, amide, clathrate, stereoisomer, enantiomer, prodrug or analogs thereof;
    wherein the $H_2S$ donor is sugammadex.

2. The method of claim 1, wherein the $H_2S$ donor is administered in a dosage of between 0.5 mg/kg and 10.0 mg/kg.

3. The method of claim 1, wherein the $H_2S$ donor is administered exactly once in a dosage period, the dosage period being between 1 day and 30 days.

4. The method of claim 3, wherein the dosage period is seven days.

5. The method of claim 1, wherein the therapeutic is administered in one of oral, intravenous, and transdermal pathways.

6. The method of claim 1, wherein the therapeutic is administered orally.

7. The method of claim 6, wherein the therapeutic has an enteric coating.

8. The method of claim 1, wherein the therapeutic is administered intravenously.

9. The method of claim 1, wherein the patient further has one of atherosclerosis, hypertension, myocardial infarction, diabetes, and cardiovascular disease, or a precondition thereof.

10. The method of claim 1, wherein the composition further comprises one of cystathionine gamma lyase or a salt, solvate, ester, amide, clathrate, stereoisomer, enantiomer, prodrug, or analogs thereof.

11. A method of treating an endothelial dysfunction related disease in a methamphetamine patient comprising:
    administering to the patient an effective dose of a pharmacologic composition;
    the composition comprising a therapeutic;
    the therapeutic including a hydrogen sulfide ($H_2S$) donor, or a salt, solvate, ester, amide, clathrate, stereoisomer, enantiomer, prodrug or analogs thereof;
    wherein the $H_2S$ donor is sugammadex.

12. The method of claim 11, wherein the related disease is one of atherosclerosis, hypertension, myocardial infarction, diabetes, and cardiovascular disease, or a precondition thereof.

13. The method of claim 12, further comprising administering a second, non-$H_2S$ donor therapeutic for the treatment of the related disease.

14. The method of claim 1, wherein the $H_2S$ donor is formulated for one of oral and peritoneal administration and is administered in a dosage of between 1.0 mg and 100.0 mg of $H_2S$ donor.

15. The method of claim 14, wherein the composition includes an exact dosage of between 5.0 and 60 mg of the $H_2S$ donor, and between 10 mg and 30 mg of the $H_2S$ donor.

16. The method of claim 14, wherein the composition further comprises cystathionine gamma lyase or a salt, solvate, ester, amide, clathrate, stereoisomer, enantiomer, prodrug, or analogs thereof.

* * * * *